(12) United States Patent
Aviles

(10) Patent No.: US 9,415,191 B2
(45) Date of Patent: *Aug. 16, 2016

(54) MEDICAL ARTICLE SECUREMENT DEVICE

(71) Applicant: C. R. Bard, Inc., Murray Hill, NJ (US)

(72) Inventor: Alejandro Aviles, Atlanta, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 149 days.

This patent is subject to a terminal disclaimer.

(21) Appl. No.: 14/293,978

(22) Filed: Jun. 2, 2014

(65) Prior Publication Data

US 2014/0276544 A1    Sep. 18, 2014

Related U.S. Application Data

(63) Continuation of application No. 13/388,291, filed as application No. PCT/US2009/054955 on Aug. 25, 2009, now Pat. No. 8,740,852.

(51) Int. Cl.
*A61M 5/32* (2006.01)
*A61M 25/02* (2006.01)

(52) U.S. Cl.
CPC ......... *A61M 25/02* (2013.01); *A61M 2025/024* (2013.01); *A61M 2025/028* (2013.01); *A61M 2025/0266* (2013.01); *A61M 2025/0273* (2013.01)

(58) Field of Classification Search
CPC .............. A61M 2025/024; A61M 2025/0266; A61M 2025/0273; A61M 2025/028; A61M 25/02
See application file for complete search history.

(56) References Cited

U.S. PATENT DOCUMENTS

| | | | |
|---|---|---|---|
| 2,525,398 A | 10/1950 | Collins | |
| 2,533,961 A | 12/1950 | Rousseau et al. | |
| 2,707,953 A | 5/1955 | Ryan | |
| 3,046,984 A | 7/1962 | Eby | |
| 3,059,645 A | 10/1962 | Hasbrouck et al. | |
| 3,064,648 A | 11/1962 | Bujan | |
| 3,167,072 A | 1/1965 | Stone et al. | |
| 3,194,235 A | 7/1965 | Cooke | |
| 3,288,137 A | 11/1966 | Lund | |
| 3,482,569 A | 12/1969 | Raaelli, Sr | |
| 3,602,227 A | 8/1971 | Andrew | |
| 3,613,663 A | 10/1971 | Johnson | |
| 3,630,195 A | 12/1971 | Santomieri | |
| 3,677,250 A | 7/1972 | Thomas | |
| 3,766,915 A | 10/1973 | Rychlik | |
| 3,782,383 A | 1/1974 | Thompson et al. | |
| 3,826,254 A | 7/1974 | Mellor | |
| 3,834,380 A | 9/1974 | Boyd | |
| 3,856,020 A | 12/1974 | Kovac | |
| 3,863,527 A | 2/1975 | Berning | |
| 3,896,527 A | 7/1975 | Miller et al. | |
| 3,900,026 A | 8/1975 | Wagner | |
| 3,901,226 A | 8/1975 | Scardenzan | |
| 3,906,946 A | 9/1975 | Nordstrom | |
| 3,973,565 A | 8/1976 | Steer | |
| 4,020,835 A | 5/1977 | Nordstrom et al. | |
| 4,057,066 A | 11/1977 | Taylor | |
| 4,059,105 A | 11/1977 | Cutruzzula et al. | |
| 4,082,094 A | 4/1978 | Dailey | |
| 4,129,128 A | 12/1978 | McFarlane | |
| 4,142,527 A | 3/1979 | Garcia | |
| 4,161,177 A | 7/1979 | Fuchs | |
| 4,165,748 A | 8/1979 | Johnson | |
| D252,822 S | 9/1979 | McFarlane | |
| 4,193,174 A | 3/1980 | Stephens | |
| 4,224,937 A | 9/1980 | Gordon | |
| 4,248,229 A | 2/1981 | Miller | |
| 4,250,880 A | 2/1981 | Gordon | |
| 4,275,143 A | 6/1981 | Sakurai | |
| 4,275,721 A | 6/1981 | Olson | |
| 4,284,076 A | 8/1981 | Hall | |
| 4,316,461 A | 2/1982 | Marais et al. | |
| 4,326,519 A | 4/1982 | D'Alo et al. | |
| 4,333,468 A | 6/1982 | Geist | |
| 4,362,156 A | 12/1982 | Feller, Jr. et al. | |
| 4,392,853 A | 7/1983 | Muto | |
| 4,397,647 A | 8/1983 | Gordon | |
| 4,449,975 A | 5/1984 | Perry | |

(Continued)

FOREIGN PATENT DOCUMENTS

CA    1 311 977    12/1992
CA    1 318 824    6/1993

(Continued)

OTHER PUBLICATIONS

International Search Report for International Application No. PCT/US2009/054955, mailed May 17, 2010, in 2 pages.
Written Opinion of the International Searching Authority for International Application No. PCT/US2009/054955, dated Feb. 25, 2012, in 9 pages.
U.S. Appl. No. 09/136,271, applicant Steven F. Bierman, filed Aug. 18, 1998.
PCT/US03/25622 filed Aug. 15, 2003 International Search Report dated Mar. 10, 2004.

(Continued)

*Primary Examiner* — Rebecca E Eisenberg
(74) *Attorney, Agent, or Firm* — Rutan & Tucker, LLP

(57) ABSTRACT

A medical article securement device holds a medical article such as a catheter hub or a connector fitting in position upon the body of a patient and inhibits movement of the medical article relative to the patient. The medical article includes an elongated body, a pair of outwardly extending wings, and a port. The securement device includes a retainer and at least one anchor pad. The retainer forms a channel into which at least a portion of the medical article is secured. The retainer includes at least one abutment that abuts against a contact point or surface on the port. The anchor pad includes an adhesive layer that is attached to both an epidural layer of a patient and at least a portion of the pair of wings.

20 Claims, 13 Drawing Sheets

(56) References Cited

U.S. PATENT DOCUMENTS

| | | |
|---|---|---|
| 4,453,933 A | 6/1984 | Speaker |
| 4,470,410 A | 9/1984 | Elliott |
| 4,480,639 A | 11/1984 | Peterson et al. |
| 4,484,913 A | 11/1984 | Swauger |
| 4,516,968 A | 5/1985 | Marshall et al. |
| 4,517,971 A | 5/1985 | Sorbonne |
| 4,563,177 A | 1/1986 | Kamen |
| 4,627,842 A | 12/1986 | Katz |
| 4,632,670 A | 12/1986 | Muller |
| 4,633,863 A | 1/1987 | Filips et al. |
| 4,645,492 A | 2/1987 | Weeks |
| 4,669,458 A | 6/1987 | Abraham et al. |
| 4,683,882 A | 8/1987 | Laird |
| 4,699,616 A | 10/1987 | Nowak et al. |
| 4,711,636 A | 12/1987 | Bierman |
| 4,737,143 A | 4/1988 | Russell |
| 4,742,824 A | 5/1988 | Payton et al. |
| 4,792,163 A | 12/1988 | Kulle |
| 4,808,162 A | 2/1989 | Oliver |
| 4,822,342 A | 4/1989 | Brawner |
| 4,826,486 A | 5/1989 | Palsrok et al. |
| 4,832,019 A | 5/1989 | Weinstein et al. |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,897,082 A | 1/1990 | Erskine |
| 4,898,587 A | 2/1990 | Mera |
| 4,919,654 A | 4/1990 | Kalt |
| 4,921,199 A | 5/1990 | Villaveces |
| 4,955,864 A | 9/1990 | Hajduch |
| 4,976,698 A | 12/1990 | Stokley |
| 4,976,700 A | 12/1990 | Tollini |
| 4,981,475 A | 1/1991 | Haindl |
| 4,986,815 A | 1/1991 | Schneider |
| 4,997,421 A | 3/1991 | Palsrok et al. |
| 5,037,397 A | 8/1991 | Kalt et al. |
| 5,069,206 A | 12/1991 | Crosbie |
| 5,073,170 A | 12/1991 | Schneider |
| 5,074,847 A | 12/1991 | Greenwell et al. |
| 5,084,026 A | 1/1992 | Shapiro |
| 5,098,399 A | 3/1992 | Tollini |
| 5,112,313 A | 5/1992 | Sallee |
| 5,116,324 A | 5/1992 | Brierley et al. |
| 5,137,519 A | 8/1992 | Littrell et al. |
| 5,147,322 A | 9/1992 | Bowen et al. |
| 5,156,641 A | 10/1992 | White |
| 5,167,630 A | 12/1992 | Paul |
| 5,192,273 A | 3/1993 | Bierman |
| 5,192,274 A | 3/1993 | Bierman |
| 5,195,981 A | 3/1993 | Johnson |
| 5,215,532 A | 6/1993 | Atkinson |
| 5,236,421 A | 8/1993 | Becher |
| 5,238,010 A | 8/1993 | Grabenkort |
| 5,266,401 A | 11/1993 | Tollini |
| 5,267,967 A | 12/1993 | Schneider |
| 5,290,248 A | 3/1994 | Bierman et al. |
| 5,292,312 A | 3/1994 | Delk et al. |
| 5,304,146 A | 4/1994 | Johnson et al. |
| 5,306,243 A | 4/1994 | Bonaldo |
| D347,060 S | 5/1994 | Bierman |
| 5,314,411 A | 5/1994 | Bierman et al. |
| 5,322,097 A | 6/1994 | Wright |
| 5,328,487 A | 7/1994 | Starchevich |
| 5,338,308 A | 8/1994 | Wilk |
| 5,342,317 A | 8/1994 | Claywell |
| 5,344,406 A | 9/1994 | Spooner |
| 5,352,211 A | 10/1994 | Merskelly |
| 5,354,282 A | 10/1994 | Bierman |
| 5,356,391 A | 10/1994 | Stewart |
| 5,370,627 A | 12/1994 | Conway |
| 5,372,589 A | 12/1994 | Davis |
| 5,380,293 A | 1/1995 | Grant |
| 5,380,395 A | 1/1995 | Uchida |
| 5,382,239 A | 1/1995 | Orr et al. |
| 5,395,344 A | 3/1995 | Beisang et al. |
| 5,402,776 A | 4/1995 | Islava |
| 5,403,285 A | 4/1995 | Roberts |
| 5,413,120 A | 5/1995 | Grant |
| 5,413,562 A | 5/1995 | Swauger |
| D359,120 S | 6/1995 | Sallee et al. |
| 5,443,460 A | 8/1995 | Miklusek |
| 5,456,671 A | 10/1995 | Bierman |
| 5,468,231 A | 11/1995 | Newman et al. |
| 5,470,321 A | 11/1995 | Forster et al. |
| D364,922 S | 12/1995 | Bierman |
| 5,480,719 A | 1/1996 | Tollini |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,527,293 A | 6/1996 | Zamierowski |
| 5,549,567 A | 8/1996 | Wolman |
| D375,355 S | 11/1996 | Bierman |
| D375,356 S | 11/1996 | Bierman |
| 5,577,516 A | 11/1996 | Schaeffer |
| 5,578,013 A | 11/1996 | Bierman |
| 5,593,395 A | 1/1997 | Martz |
| D377,831 S | 2/1997 | Bierman |
| 5,605,546 A | 2/1997 | Wolzinger et al. |
| 5,637,098 A | 6/1997 | Bierman |
| 5,664,581 A | 9/1997 | Ashley |
| 5,681,290 A | 10/1997 | Alexander |
| 5,685,859 A | 11/1997 | Kornerup |
| 5,686,096 A | 11/1997 | Khan et al. |
| 5,690,616 A | 11/1997 | Mogg |
| 5,693,032 A | 12/1997 | Bierman |
| 5,702,371 A | 12/1997 | Bierman |
| 5,722,959 A | 3/1998 | Bierman |
| 5,728,053 A | 3/1998 | Calvert |
| 5,755,225 A | 5/1998 | Hutson |
| 5,800,402 A | 9/1998 | Bierman |
| 5,800,410 A | 9/1998 | Gawreluk |
| 5,810,781 A | 9/1998 | Bierman |
| D399,954 S | 10/1998 | Bierman |
| 5,827,230 A | 10/1998 | Bierman |
| 5,827,239 A | 10/1998 | Dillon et al. |
| 5,833,666 A | 11/1998 | Davis et al. |
| 5,833,667 A | 11/1998 | Bierman |
| 5,855,591 A | 1/1999 | Bierman |
| 5,885,254 A | 3/1999 | Matyas |
| 5,897,519 A | 4/1999 | Shesol et al. |
| 5,911,707 A | 6/1999 | Wolvek et al. |
| 5,916,200 A | 6/1999 | Eppley et al. |
| 5,947,931 A | 9/1999 | Bierman |
| 6,050,934 A | 4/2000 | Mikhail et al. |
| D425,619 S | 5/2000 | Bierman |
| 6,067,985 A | 5/2000 | Islava |
| 6,099,509 A | 8/2000 | Brown et al. |
| 6,113,577 A | 9/2000 | Hakky et al. |
| 6,132,398 A | 10/2000 | Bierman |
| 6,132,399 A | 10/2000 | Shultz |
| 6,213,979 B1 | 4/2001 | Bierman |
| 6,224,571 B1 | 5/2001 | Bierman |
| 6,228,064 B1 | 5/2001 | Abita et al. |
| 6,231,547 B1 | 5/2001 | O'Hara |
| 6,231,548 B1 | 5/2001 | Bassett |
| 6,258,066 B1 | 7/2001 | Urich |
| 6,283,945 B1 | 9/2001 | Bierman |
| 6,287,281 B1 | 9/2001 | Nishtala et al. |
| 6,290,676 B1 | 9/2001 | Bierman |
| 6,361,523 B1 | 3/2002 | Bierman |
| 6,375,639 B1 | 4/2002 | Duplessie |
| 6,413,240 B1 | 7/2002 | Bierman et al. |
| 6,428,515 B1 | 8/2002 | Bierman et al. |
| 6,428,516 B1 | 8/2002 | Bierman et al. |
| 6,436,073 B1 | 8/2002 | Von Teichert |
| 6,447,485 B2 | 9/2002 | Bierman |
| 6,447,486 B1 | 9/2002 | Tollini |
| 6,471,676 B1 | 10/2002 | DeLegge et al. |
| 6,482,183 B1 | 11/2002 | Pausch |
| 6,488,664 B1 | 12/2002 | Solomon et al. |
| 6,491,664 B2 | 12/2002 | Bierman |
| 6,500,154 B1 | 12/2002 | Hakky et al. |

(56) References Cited

U.S. PATENT DOCUMENTS

| | | |
|---|---|---|
| D469,530 S | 1/2003 | Gomez |
| D470,936 S | 2/2003 | Bierman |
| 6,517,522 B1 | 2/2003 | Bell |
| 6,551,285 B1 | 4/2003 | Bierman |
| 6,572,588 B1 | 6/2003 | Bierman et al. |
| 6,582,403 B1 | 6/2003 | Bierman et al. |
| 6,616,635 B1 | 9/2003 | Bell |
| 6,626,890 B2 | 9/2003 | Nguyen et al. |
| 6,652,487 B1 | 11/2003 | Cook |
| 6,663,600 B2 | 12/2003 | Bierman et al. |
| 6,689,104 B2 | 2/2004 | Bierman |
| D492,411 S | 6/2004 | Bierman |
| 6,770,055 B2 | 8/2004 | Bierman et al. |
| 6,786,892 B2 | 9/2004 | Bierman |
| 6,809,230 B2 | 10/2004 | Hancock et al. |
| 6,827,705 B2 | 12/2004 | Bierman |
| 6,827,706 B2 | 12/2004 | Tollini |
| 6,827,707 B2 | 12/2004 | Wright et al. |
| 6,834,652 B2 | 12/2004 | Altman |
| 6,837,875 B1 | 1/2005 | Bierman |
| 6,866,652 B2 | 3/2005 | Bierman |
| D503,977 S | 4/2005 | Bierman |
| 6,951,550 B2 | 10/2005 | Bierman |
| 6,972,003 B2 | 12/2005 | Bierman |
| 6,979,320 B2 | 12/2005 | Bierman |
| 6,981,969 B2 | 1/2006 | Chavez et al. |
| 7,014,627 B2 | 3/2006 | Bierman |
| 7,018,362 B2 | 3/2006 | Bierman |
| 7,070,580 B2 | 7/2006 | Nielsen |
| 7,090,660 B2 | 8/2006 | Roberts et al. |
| D528,206 S | 9/2006 | Bierman |
| 7,153,291 B2 | 12/2006 | Bierman |
| 7,354,421 B2 | 4/2008 | Bierman |
| 7,377,472 B2 | 5/2008 | Brown et al. |
| 7,413,561 B2 | 8/2008 | Raulerson et al. |
| 7,799,001 B2 | 9/2010 | Bierman |
| 8,251,956 B2 | 8/2012 | Bierman et al. |
| 8,357,124 B2 | 1/2013 | Bierman |
| 8,734,400 B2 | 5/2014 | Ciccone |
| 8,740,852 B2 | 6/2014 | Aviles |
| 2001/0011164 A1 | 8/2001 | Bierman |
| 2002/0068904 A1 | 6/2002 | Bierman et al. |
| 2002/0099360 A1 | 7/2002 | Bierman |
| 2002/0133121 A1 | 9/2002 | Bierman |
| 2003/0055382 A1 | 3/2003 | Schaeffer |
| 2003/0229313 A1 | 12/2003 | Bierman |
| 2004/0102736 A1 | 5/2004 | Bierman |
| 2004/0111067 A1 | 6/2004 | Kirchhofer |
| 2004/0138624 A1 | 7/2004 | Bierman |
| 2004/0204685 A1 | 10/2004 | Wright et al. |
| 2005/0182367 A1 | 8/2005 | Walborn |
| 2005/0215953 A1 | 9/2005 | Rossen |
| 2005/0251157 A1 | 11/2005 | Saadat et al. |
| 2005/0288635 A1 | 12/2005 | Davis et al. |
| 2006/0015076 A1 | 1/2006 | Heinzerling et al. |
| 2006/0064063 A1 | 3/2006 | Bierman |
| 2006/0135944 A1 | 6/2006 | Bierman |
| 2006/0184127 A1 | 8/2006 | Bierman |
| 2006/0184129 A1 | 8/2006 | Bierman |
| 2006/0217669 A1 | 9/2006 | Botha |
| 2006/0247577 A1 | 11/2006 | Wright |
| 2006/0264836 A1 | 11/2006 | Bierman |
| 2006/0270995 A1 | 11/2006 | Bierman |
| 2007/0173766 A1 | 7/2007 | Bierman |
| 2008/0125718 A1 | 5/2008 | Tsuchiya et al. |
| 2009/0143740 A1 | 6/2009 | Bierman et al. |
| 2010/0179482 A1 | 7/2010 | Wright et al. |

FOREIGN PATENT DOCUMENTS

| | | |
|---|---|---|
| EP | 0064284 A2 | 11/1982 |
| EP | 0356683 | 3/2000 |
| EP | 2470251 B1 | 12/2014 |
| FR | 2381529 A1 | 9/1978 |
| FR | 2 922 458 | 4/2009 |
| GB | 2086466 A | 5/1982 |
| GB | 2211417 A | 7/1989 |
| WO | 8001458 A1 | 7/1980 |
| WO | 9412231 A1 | 6/1994 |
| WO | WO 94/21319 | 9/1994 |
| WO | WO 97/15337 | 5/1997 |
| WO | WO 99/55409 | 11/1999 |
| WO | 00/48658 A1 | 8/2000 |
| WO | WO 2004/016309 | 2/2004 |
| WO | 2004022140 A1 | 3/2004 |
| WO | 2007024900 A2 | 3/2007 |
| WO | 2007117655 A2 | 10/2007 |
| WO | 2008151047 A1 | 12/2008 |
| WO | WO 2011/025478 | 3/2011 |
| WO | 2011133818 A1 | 10/2011 |

OTHER PUBLICATIONS

PCT/US2009/054955 filed Aug. 25, 2009 International Search Report and Written Opinion dated May 17, 2010.

PCT/US2009/057566 filed Sep. 18, 2009 International Search Report and Written Opinion dated Nov. 16, 2009.

PCT/US2010/044016 filed Jul. 30, 2010 International Preliminary Report on Patentability dated Feb. 5, 2013.

PCT/US2010/044016 filed Jul. 30, 2010 International Search Report and Written Opinion dated Sep. 24, 2010.

U.S. Appl. No. 11/837,472, filed Aug. 10, 2007, Non-Final Office Action dated Oct. 2, 2015.

U.S. Appl. No. 11/837,472, filed Aug. 10, 2007, Final Office Action dated Jun. 11, 2015.

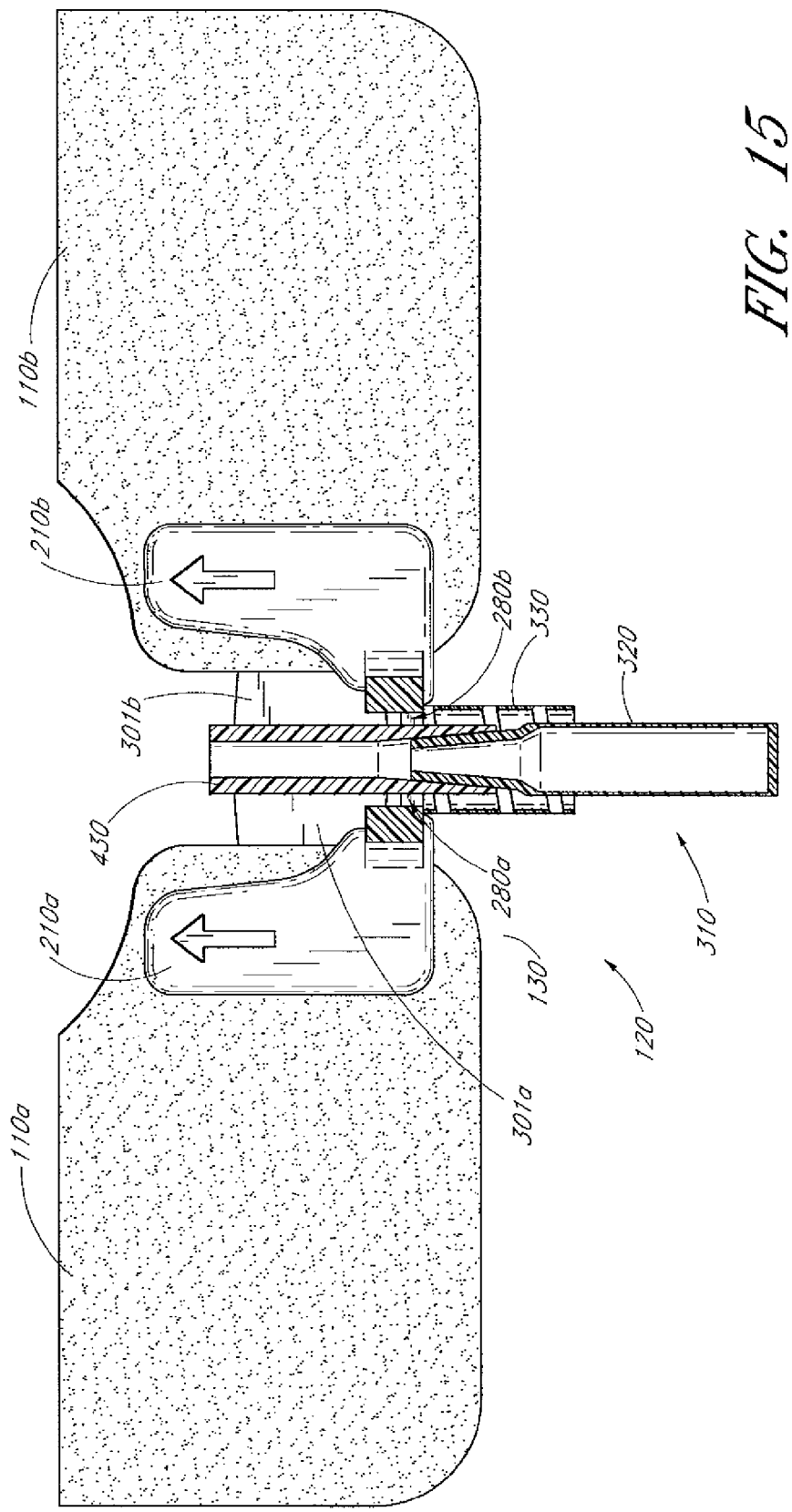

MEDICAL ARTICLE SECUREMENT DEVICE

RELATED APPLICATIONS

This application is a continuation of U.S. patent application Ser. No. 13/388,291, filed on May 25, 2012, now U.S. Pat. No. 8,740,852, which is the national phase under 35 U.S.C. §371 of prior PCT International Application No. PCT/US2009/054955, filed on Aug. 25, 2009. Each of the aforementioned applications is incorporated by reference herein in its entirety, and each is hereby expressly made a part of this specification.

BACKGROUND OF THE INVENTION

1. Field of the Invention

This invention relates to a securement system used to attach a medical line to a patient.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line can be secured to the patient in a variety of ways. Most commonly, this involves taping the catheter or medical line to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin in the area around the dressing. Such repeated applications of tape over the catheter or medical line can additionally lead to the build up of adhesive residue on the outer surface of the catheter or medical line. This residue can result in contaminants adhering to the catheter itself, increasing the likelihood of infection of the insertion site. This residue can also make the catheter or medical line stickier and more difficult to handle for healthcare providers.

SUMMARY OF THE INVENTION

The systems and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Preferred Embodiments" one will understand how the features of this invention provide several advantages over traditional catheter securement systems.

One aspect of the present invention is a medical article securement system that comprises a medical article, at least one anchor pad, and a retainer. The medical article comprises an elongated body having a longitudinal axis, a pair of wings extending away from the elongated body, and a port disposed on the elongated body and forming a contact surface. The port and the pair of wings are disposed along the longitudinal axis of the elongated body at the same general location. The at least one anchor pad includes a lower adhesive surface for attaching to both an epidural layer of a patient and at least a portion of the pair of wings. The retainer comprises a body member, at least one abutment, and at least one support. The body member has a channel formed therethrough about a channel axis, the channel having a longitudinal length for receiving at least a portion of the elongated body and permitting access to the port at least when the medical article is secured within the channel. The body member also has a longitudinal access opening disposed on an underside of the body member to allow at least ingress of the portion of the elongated body into the channel. The at least one abutment extends generally normal to the channel axis and is configured to abut the contact surface on the port so as to inhibit longitudinal movement of the medical article relative to the retainer in at least one direction. The at least one support is disposed on the underside of the body member and to a side of the access opening opposite the channel access. The support is attached to the at least one anchor pad.

Another aspect of the invention is a system for securing a medical article to a patient comprising a medical article, a retainer, and a pair of anchor pads. The medical article comprises an elongated body having a longitudinal axis, a pair of wings extending in opposite lateral directions from the elongated body, and a port disposed on the elongated body and extending generally in a transverse direction. The port is generally aligned with the pair of wings along the longitudinal axis. The retainer comprises a body member that has a channel formed therethrough about a channel axis. The channel receives at least a portion of the elongated body and permits access to the port at least when the medical article is received within the channel. The body member has a longitudinal access opening disposed on an underside of the body member to allow at least ingress of the portion of the elongated body into the channel. A pair of supports is disposed on the underside of the body member and to the sides of the access opening opposite the channel axis. A pair of anchor pads is attached to the pair of supports. The anchor pads include a lower adhesive surface for attaching to both an epidural layer of a patient and at least a portion of each wing such that the wings are secured relative to both the epidural layer of the patient and the retainer.

Yet another aspect of the invention is a method for securing a medical article to a patient. The method comprises providing a medical article comprising an elongated body having a longitudinal axis, a pair of wings and a port extending away from the elongated body at generally the same location along the longitudinal axis, the port defining a contact surface disposed on a distal side of the port. The method also comprises providing a retainer comprising a body member and two anchor pads, the body member having a channel formed therethrough, the channel being configured to receive the medical article, and at least one abutment extending generally normal to the channel. The method also comprises pressing the medical article into the channel through an opening formed on the underside of the retainer such that the port remains accessible and the medical article is inhibited from moving in both transverse and lateral directions, abutting the contact surface on the port against the at least one abutment on the retainer so as to inhibit longitudinal motion of the medical article relative to the retainer in a first longitudinal direction, and adhering the anchor pads to at least a portion of the pair of wings so as to inhibit longitudinal motion of the medical article relative to the retainer in a second longitudinal direction.

These and other features of the present invention will become readily apparent to those skilled in the art from the following detailed description of the preferred embodiments, which refers to the attached figures. The invention is not limited, however, to the particular embodiments that are disclosed.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of the drawings.

FIG. 15 is a cross-section through the securement system and medical article taken along line 15-15 of FIG. 14.

DETAILED DESCRIPTION OF THE PREFERRED EMBODIMENTS

The following description and the accompanying figures, which describe and show the preferred embodiments, are made to demonstrate several possible configurations that a securement system can take to include various aspects and features of the invention. The illustrated embodiments are shown in use with either one or both of an illustrative example of a catheter hub and an illustrative example of a connector fitting (e.g., an extension set) with a spin nut for connection to the catheter hub. The illustration of the securement device in this context is not intended to limit the disclosed aspects and features of the invention to the specified embodiments or to usage only with the illustrated connector or hub. Those of skill in the art will recognize that the disclosed aspects and features of the invention are not limited to any particular embodiment of a securement system, and securement systems, which include one or more of the inventive aspects and features herein described, can be designed for use with a variety of medical articles.

Figure 1:
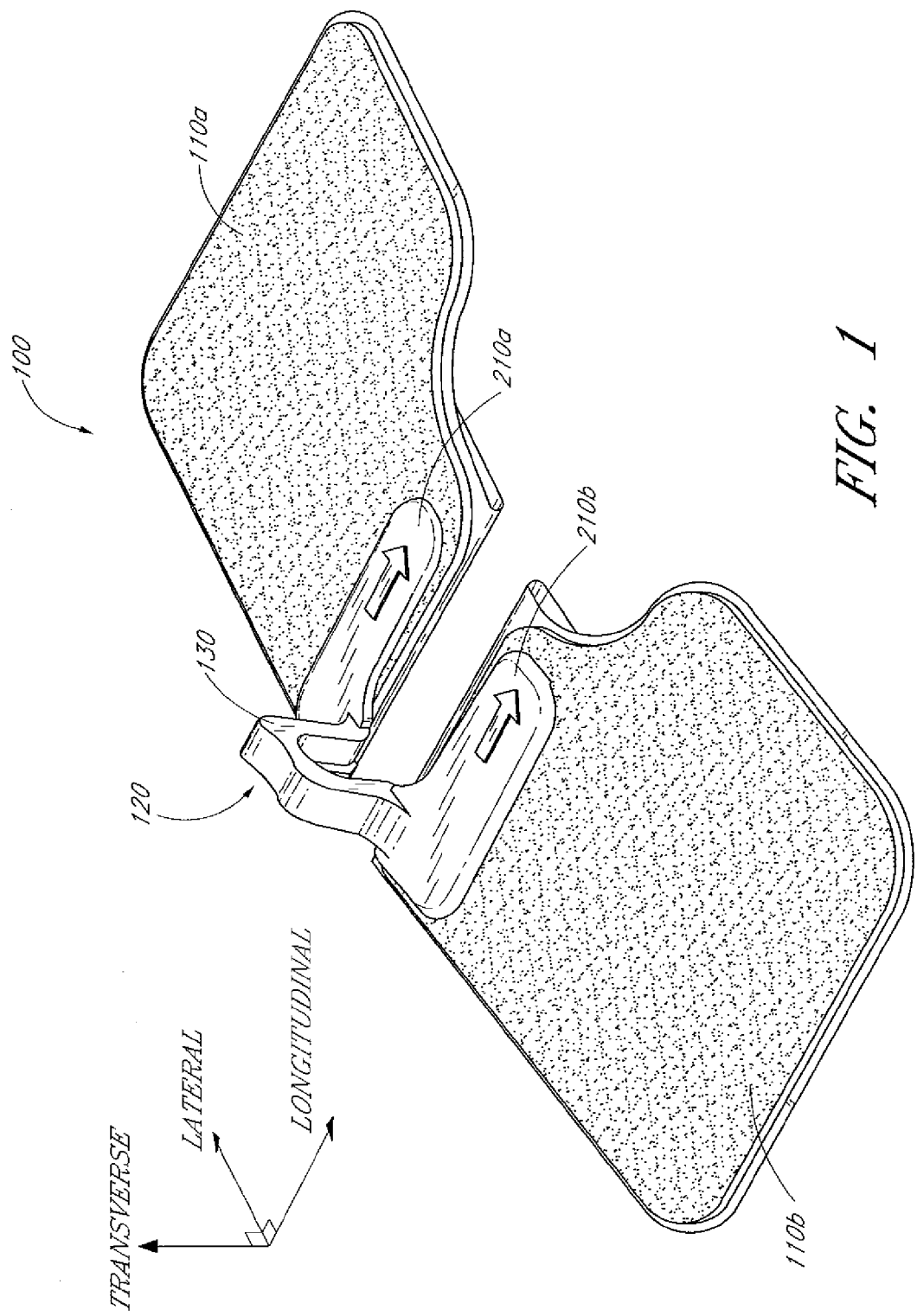
FIG. 1 is a perspective view of a securement device configured in accordance with a preferred embodiment of the present invention.

To assist in the description of these components of the securement system, the following coordinate terms are used (see FIG. 1). A "longitudinal axis" is generally parallel to a portion of the catheter hub, the connector fitting or other medical article retained by the securement system, as well as parallel to the axis of a channel of the retainer, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or connector fitting, and therefore is substantially synonymous with the term "longitudinal" as used herein. Also, the terms "proximal" and "distal", which are used to describe the present securement system, are used consistently with the description of the exemplary applications (e.g., the illustrative examples of the use applications). Thus, proximal and distal are used in reference to the center of the patient's body. The terms "upper," "lower," "top," "bottom," "underside," "upperside" and the like, which also are used to describe the present securement system, are used in reference to the illustrated orientation of the embodiment. For example, the term "upperside" is used to describe the portion of the retainer that is located above a lateral axis that passes through the axis of the channel. The term "underside" is used to describe the portion of the retainer that is located below a lateral axis that passes through the axis of the channel. Brief introductions to some of the features, which are common to the described embodiments of the securement systems, are now described. In the illustrated embodiment, the arrows on the securement device point in the direction toward the insertion site (e.g., in the proximal direction).

The preferred embodiments of the present invention advantageously provide a multi-point medical line securement system. The medical article preferably has a pair of wings. The wings of the medical article cooperate with a first portion of the securement device while the body of the medical article cooperates with a second portion of the securement device to arrest movement of the medical article when the medical article is placed within the retainer.

In each of the embodiments described below, the retainer has a body member which includes an inverted channel formed therethrough. The inverted channel has a longitudinal access opening located on an underside of the retainer to allow ingress and/or egress of the medical article. The medical article is installed or removed from the underside of the retainer via this access opening. Such an arrangement allows the healthcare provider to align at least a portion of the medical article with the retainer prior to fixing the retainer to the patient's skin. In this way, the inverted channel retains a portion of the medical article.

The retainer includes at least one abutment (preferably an abutment surface) that cooperates with at least one contact point or surface on the medical article. The one or more abutments of the retainer extend generally normal to the axis of the channel and can be, for example, but without limitation a surface, a wall of a slot, a ridge, a protuberance, or similar structures. The abutment cooperates with the one or more contact points or surfaces of the medical article to inhibit longitudinal movement of the medical article through the channel. For example, the abutment could be a surface on the proximal end of the retainer that acts against at least a portion of a port or similar member extending generally in a transverse direction from the medical article. In this way, the medical article will be limited in its distal movement (e.g., movement away from the patient) once the port contacts or abuts against the proximal end of the retainer.

The retainer of each embodiment described below further includes at least one support that is preferably disposed on the underside of the retainer at a position lower than the access opening. Each support in the illustrated embodiments includes a left/right mounting wing. The wings are preferably integral to the body member and are attached to left and right anchor pads. Lower surfaces of the left and right anchor pads contact the wings of the medical article independent from the body of the medical article contacting the channel. In this way, the wings of the secured medical article are disposed between the lower surfaces of the left and/or right anchor pads and the patient's skin to provide a secondary or redundant point of securement between the medical article and the securement device.

To facilitate a complete understanding of the illustrated embodiment, the remainder of the detailed description describes the securement system with reference to the attached figures, wherein like elements among the embodiments are referenced with like numerals throughout the following description.

Figure 2:
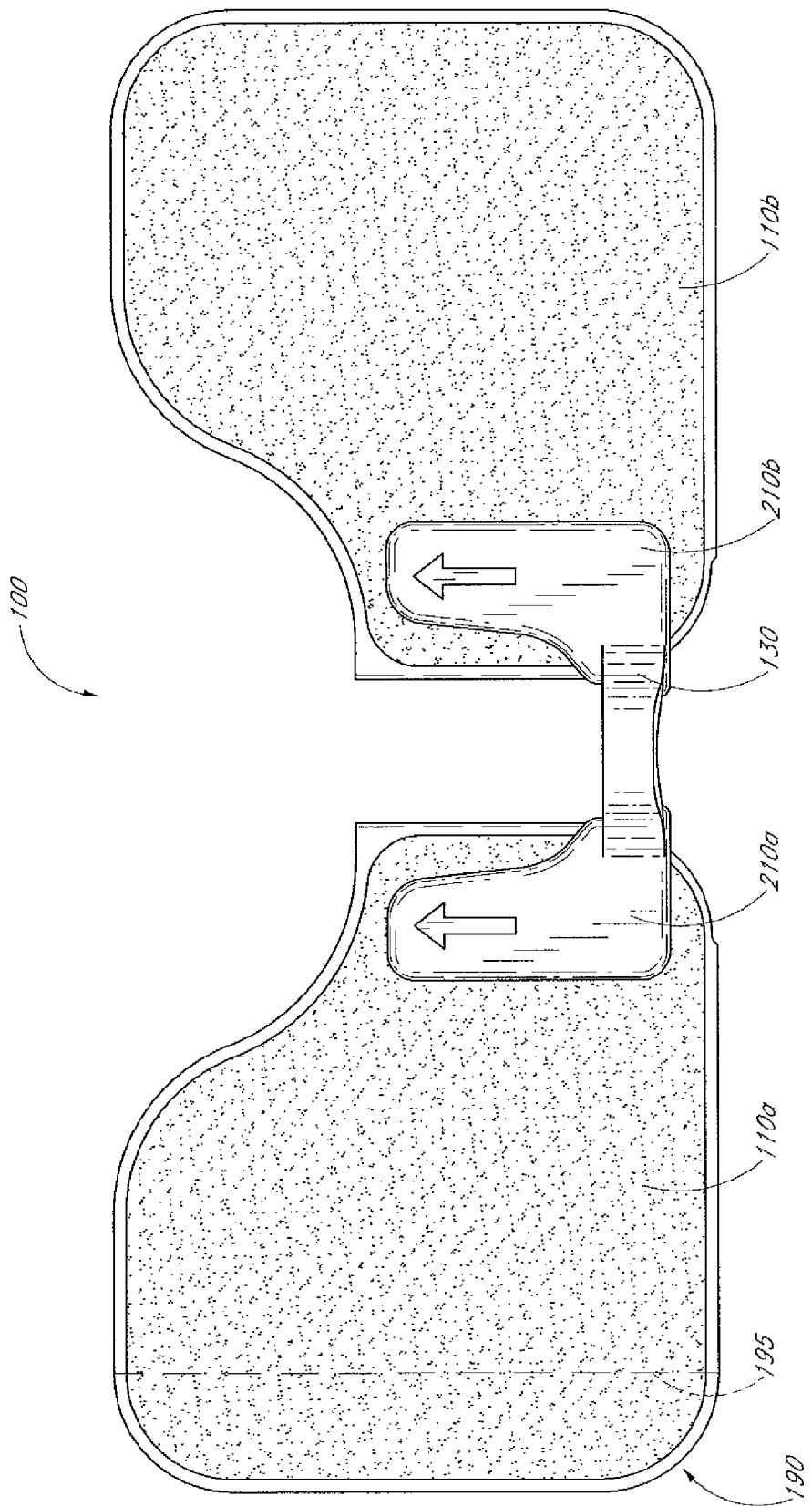
FIG. 2 is a top plan view of the securement system of FIG. 1 that includes a retainer and anchor pads.

FIG. 1 is a perspective view of a securement system 100 configured in accordance with an embodiment of the present invention and FIG. 2 is a top plan view of the securement system 100 of FIG. 1. As shown in FIGS. 1 and 2, the illustrated securement system 100 comprises three main components: two anchor pads 110(a), 110(b) and a retainer 120. The illustrated retainer 120 includes a left footing/mounting support 210(a) and right footing/mounting support 210(b). Each mounting support 210(a), 210(b) is disposed upon the respective one of the anchor pads 110(a), 110(b). The mounting supports 210(a), 210(b) extend in a lateral direction away from a center of the retainer 120.

As noted above, the securement system 100 can form a component of a catheterization system that also includes one or more medical articles, such as connector fittings, catheters, hubs, catheter adaptors, fluid supply lines, or other articles suitable for securement via the anchor pads and retainer. An opening in the retainer 120 is aligned with the medical article. The medical article is inserted between the anchor pads 110(a), 110(b), through the opening, and into the retainer 120. The anchor pads 110(a), 110(b) may include an adhesive disposed upon the bottom surface of the pads. The medical article may include a pair of laterally extending members/wings and at least a portion of each wing may be attached to the adhesive layers of pads 110(a), 110(b). The anchor pads 110(a), 110(b) may then be secured to the skin of the patient via the adhesive surfaces. In this way, the retainer 120 secures the medical article to the patient. Thus, the securement system 100 at least restricts, if not prevents, longitudinal, transverse, lateral, and rotational movement of the retained section of the medical article relative to the retainer 120. The embodiment illustrated is preferably for use with a catheter adapter or hub, as described with reference to FIGS. 10-15. The embodiments of the anchor pad and the retainer are described in more detail below.

Anchor Pad

Figure 3:
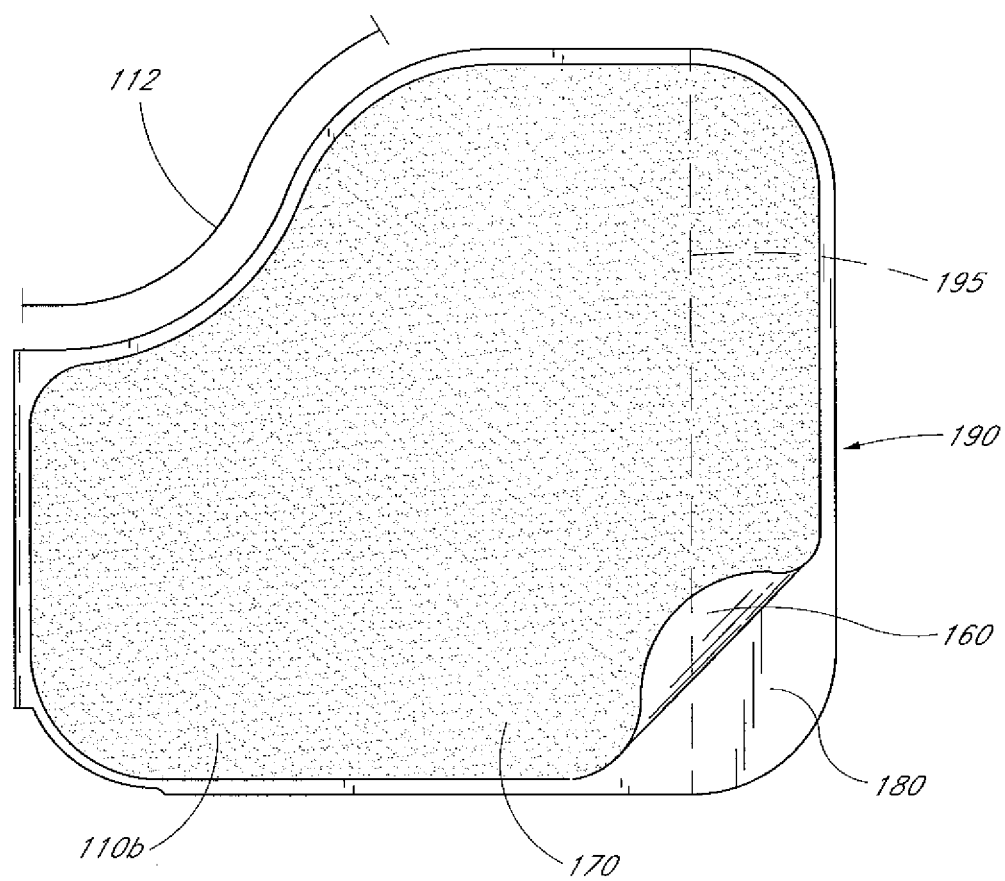
FIG. 3 is a top plan view of a right anchor pad from FIG. 2.
Figure 4:
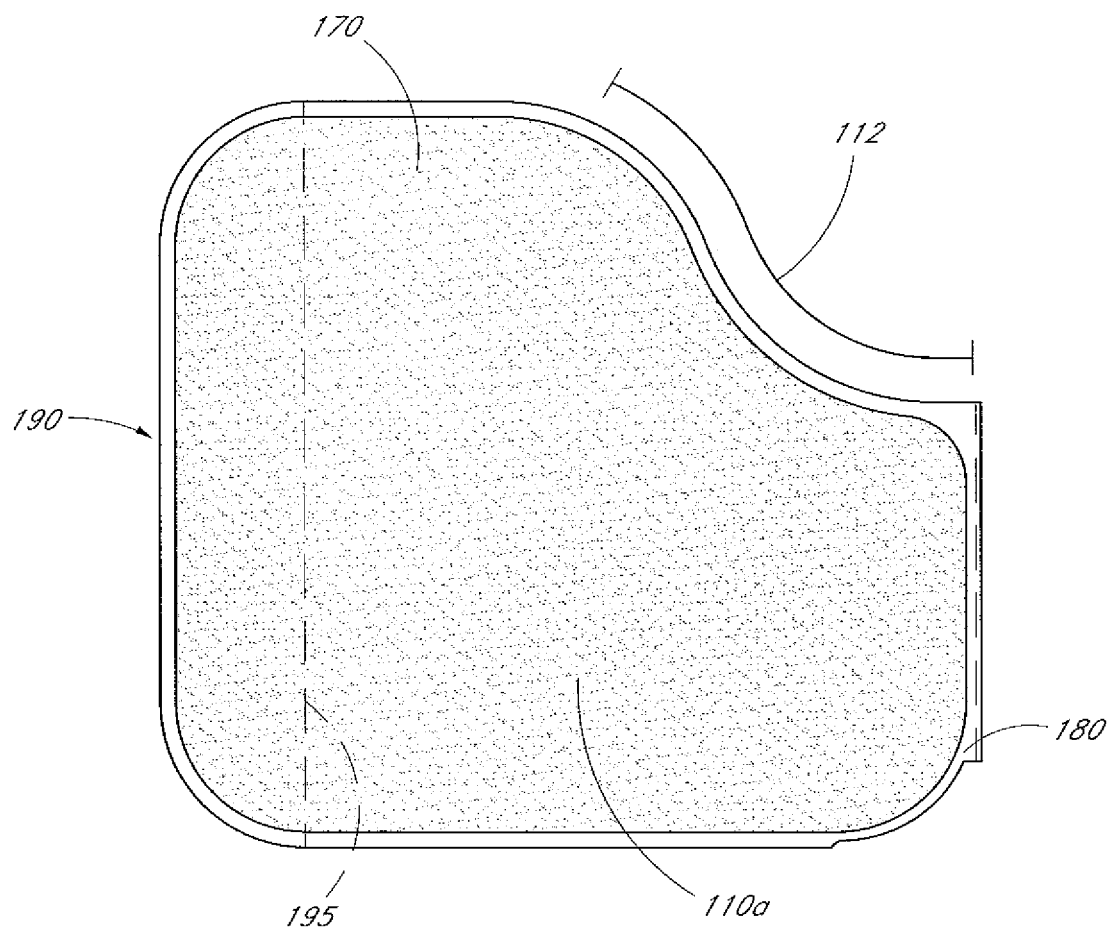
FIG. 4 is a top plan view of a left anchor pad from FIG. 2.

FIGS. 3 and 4 illustrate the anchor pads 110(b), 110(a), respectively, apart from the rest of the securement system 100 of FIGS. 1 and 2. The general structure of each anchor pads 110(a), 110(b) comprises a generally rectangular shape with a scalloped region 112 located at a corner of each anchor pad. The scalloped configuration eases the process of aligning the securement device 100 with a catheter insertion site in the patient's skin. Although only a single shape of the anchor pad is illustrated in FIGS. 3 and 4, those of skill in the art will recognize that a variety of shapes can be used.

Each anchor pad 110 desirably comprises a laminate structure with an upper plastic, paper or foam layer (e.g., closed-cell polyethylene foam) and a lower adhesive layer. The lower adhesive layer constitutes a lower surface 160 of the anchor pad. The lower surface 160 desirably is a medical-grade adhesive and can be either diaphoretic or nondiaphoretic, depending upon the particular application. Such foam with an adhesive layer is available commercially from Avery Dennison of Painsville, Ohio. While not illustrated, the anchor pads 110(a), 110(b) can include suture holes in addition to the adhesive layer to further secure the anchor pad to the patient's skin.

In other variations, a hydrocolloid adhesive or zinc oxide-based adhesive can advantageously be used upon the anchor pads 110(a), 110(b) for attaching the anchor pads to wings extending from the medical article and to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

In another variation, each anchor pad 110(a), 110(b) comprises a laminate structure with an upper woven layer and a lower adhesive layer. The upper layer can be polyester or other suitable polymer or textile materials. One particular suitable material is a woven polyester available commercially under the name "Tricot" from Tyco. The lower adhesive layer constitutes the lower surface 160 of the anchor pad. The lower surface desirably is a medical-grade adhesive and can be either diaphoretic or nondiaphoretic, depending upon the particular application.

A surface of the upper foam layer constitutes an upper surface 170 of the anchor pads 110(a), 110(b). The upper surface 170 can be roughened by corona-treating the foam with a low electric charge. The roughened or porous upper surface can improve the quality of the adhesive joint (which is described below) between the mounting wings 210 and the anchor pads 110. In a further variation, the flexible anchor pad can comprise an upper paper or other woven or nonwoven cloth or plastic layer in lieu of a roughened upper foam surface.

The anchor pads 110(a), 110(b) preferably are arranged with respect to the retainer 120 such that the tip of the medical article does not extend beyond the front edge of the anchor pads 110(a), 110(b) when the medical article is properly inserted within the retainer 120. The healthcare provider can be instructed to generally align the medical article tip with the front edges of the anchor pads 110(a), 110(b) before inserting the medical article into the retainer 120.

As illustrated in FIG. 3, a removable paper or plastic release liner 180 desirably covers the adhesive lower surface 160 before use. The liner 180 preferably resists tearing and desirably is divided into a plurality of pieces to ease attachment of the pad to a portion of a laterally extending wing and to a patient's skin.

The liner 180 comprises a folded over portion to define a pull tab 190. The pull tab can be utilized to remove the paper or plastic release liner 180 from their adhesive lower surface 160 before use. A healthcare provider uses the pull tab 190 by grasping and pulling on it so that the liner 180 is separated from the lower surface 160. The pull tab 190 overcomes any requirement that the healthcare provider pick at a corner edge or other segment of the liner in order to separate the liner from the adhesive layer.

The pull tab 190 of course can be designed in a variety of configurations. For example, the pull tab 190 can be located along a center line of the anchor pad 110; or alternatively, the pull tab can be located along any line of the anchor pad 110 in order to ease the application of the anchor pad onto the patient's skin at a specific site. For example, an area of a patient's skin with an abrupt bend, such as at a joint, can require that the pull tab 190 be aligned toward one of the lateral ends of the anchor pad 110 rather than along the center line. In the embodiment illustrated in FIGS. 3 and 4, the pull tab 190 extends from a bottom surface of the anchor pads 110(a), 110(b) and along an outer line 195.

The fold that forms the pull tab 190 preferably occurs laterally beyond the inner (medial) edge on each anchor pad 110(a), 110(b), as best seen in FIG. 2, rather than at the inner edge of the anchor pad 110(a), 110(b). Thus, the spacing between the folds of the release liners 180 is less than the spacing between the inner edges of the anchor pads 110(a), 110(b). The projection of the release liner beyond the anchor pad inner edge provides an area onto which any adhesive, which is used to attach the retainer to the anchor pad, can run while lessening the occurrence of such adhesive contacting the fold. Cracks often occur at the fold and presence of adhesive in such cracks can create delimitation of the release liner and incomplete removal of the release liner when peeled away from the corresponding anchor pad 110(a), 110(b).

Additionally, the distal side of each release liner is cut to increase a "view window" through which a healthcare provider can see when aligning the retainer over the medical article (e.g., the catheter hub and/or the connector fitting). Preferably, the resulting relief originates from the inner edge of the release liner generally at a right angle thereto and then transitions into a shape that generally matches the shape of the adjacent region of corresponding anchor pad 110(a), 110(b). The initial right-angle cut of this relief reduces instances of the release liner ripping when properly pulled in the lateral direction away from the retainer 120.

Retainer

Figure 5:
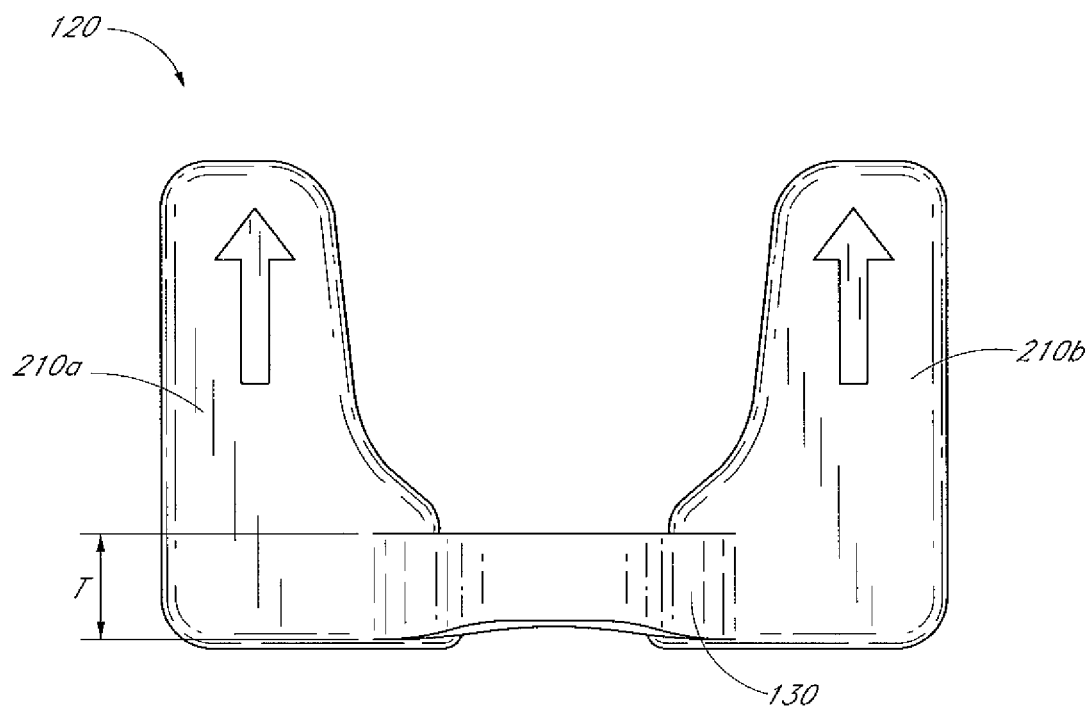
FIG. 5 is a top plan view of the retainer shown in FIG. 2.

An embodiment of the retainer 120 is described with reference to FIGS. 5-9. FIG. 5 is a top plan view of the retainer 120. The retainer 120 preferably limits rotation of an installed catheter hub as well as arrests movement of the catheter hub in the longitudinal, lateral and transverse directions. The interactions between the wings on the catheter hub and a lower surface of the retainer 120 and between the elongated body of the catheter hub and one or more abutments on the retainer 120 together provide this feature. This multi-point securement function provided by the retainer 120 enhances securement between the catheter hub and retainer 120 when compared to traditional single-point securement structures.

Figure 6:
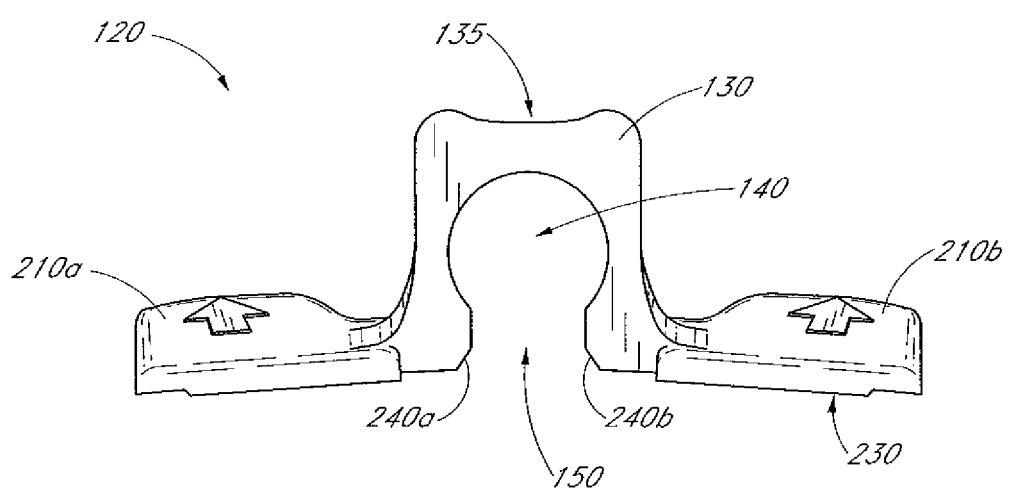
FIG. 6 is a back side view of the retainer of FIG. 5.
Figure 7:
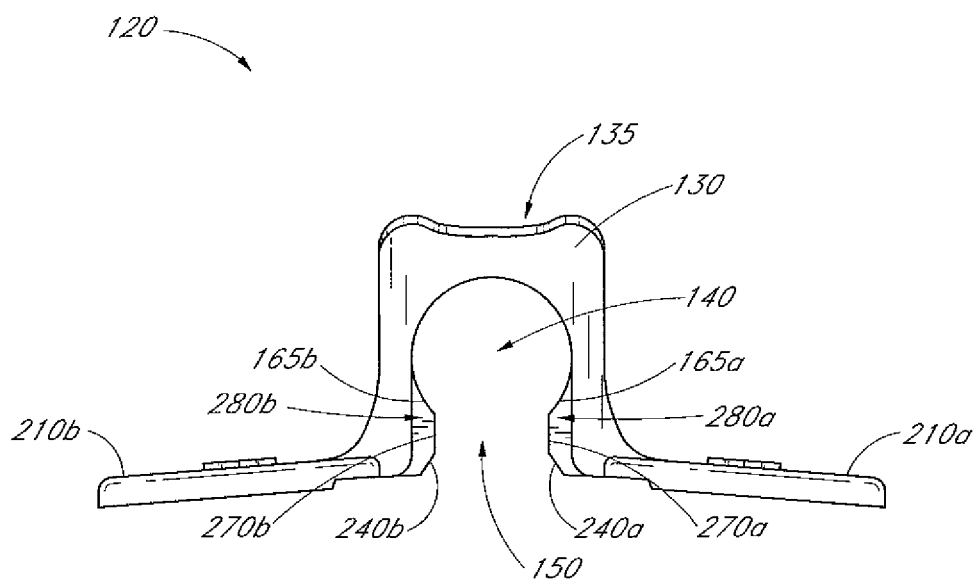
FIG. 7 is a front side view of the retainer of FIG. 5.
Figure 8:
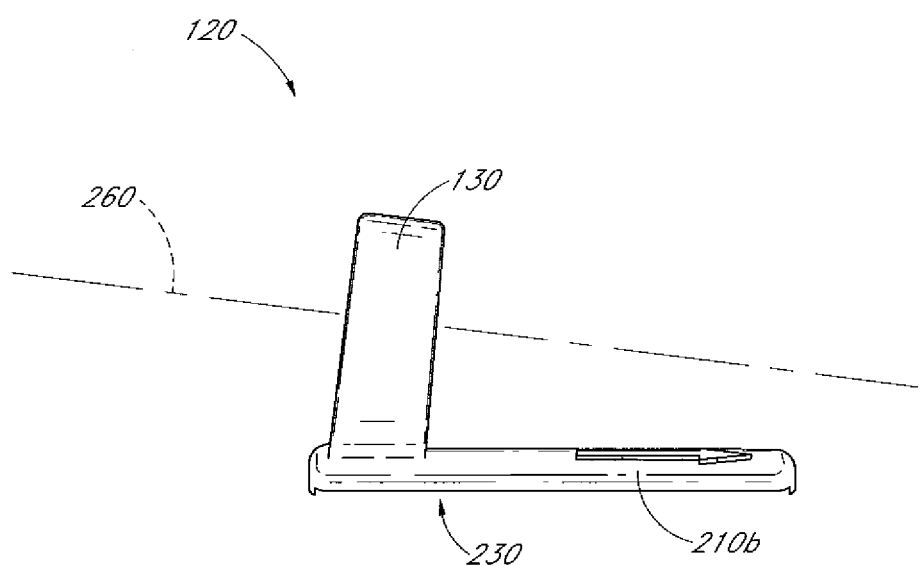
FIG. 8 is a side view of the retainer of FIG. 5.

FIGS. 6 and 7 are a back side view and front side view, respectively, of the retainer 120 from FIG. 5 and illustrate a body member 130 and footings/side mounting supports 210(a), 210(b). The footings/side mounting supports 210(a), 210(b) extend in an outward direction from either side of the body member. As shown in FIG. 8, the body member 130 is elongated in the longitudinal direction and comprises a generally parallelepiped shape. While it may be advantageous for the parallelepiped shaped portion of the body member 130 to be of a sufficient length to independently provide stability to the retained portion of the medical article along its length, it is not required. For example, the length of the body member 130, and more particularly the length of the portion of the body member 130 which receives the elongated medical article, may be relatively short but the retainer 120 still stabilizes the catheter hub via the interaction between the wings of the catheter hub and the lower surfaces of the anchor pads. In this way, even when the retained portion is relatively short the interaction between the wings of the medical article and the anchor pads enhances the retainers 120 ability to inhibit the rocking of the secured medical article.

With reference to FIGS. 6 and 7, the inner side of the body member 130 faces towards the patient's skin when in use and preferably defines an inverted central channel 140. The inverted channel 140 extends on the underside of the body member 130 in a longitudinal direction for receiving a section of the catheter hub in the illustrated embodiment.

The channel 140 is capable of receiving a portion or length of the medical article and is generally configured to house, to preferably grip, and to secure this portion of the medical article. In one embodiment, the channel 140 is configured to house, grip, and secure a portion of a catheter hub between an outwardly extending port and an extension set hub or cap. In the illustrated embodiment (see FIGS. 5 through 8), the central channel 140 has a generally semi-circular cross-sectional shape. An inner surface contour of the central channel 140 preferably is selected depending on the geometry of the portion of the medical article to be retained. For example, in a retainer 120 that is configured to retain a portion of a medical article that has a constant outer diameter, the central channel 140 preferably has a constant radius along its length. In contrast, in a retainer 120 configured to retain a portion of a medical article that has a tapering outer surface, the central channel 140 has a tapering inner surface and a radius that varies along the channel length.

Additional embodiments of the central channel 140 of the retainer can comprise a plurality of different radii and/or tapering regions. In this way, the size and shape of the central channel 140 can be chosen to match or to approximate the size and shape of the medical article or portion thereof, e.g., the catheter hub, to be retained. By matching the inner surface contour of the central channel 140 to the outer surface of the secured portion of a medical article, a more effective securement may be achieved. In addition or in the alternative, effective securement can also be achieved by the engagement of one or more abutment surfaces of the retainer with one or more contact surfaces on the medical article. Each abutment surface can cooperate with a contact surface on the medical article to inhibit movement of the medical article relative to the retainer. Exemplary abutment surfaces and contact surfaces are described below with reference to FIGS. 10-12.

Although the central channel 140 can be formed in various shapes depending upon the desired application (e.g., depending upon a shape of the retained portion of the medical article for which the retainer is designed to be used), the central channel 140 desirably has a sufficient length in the longitudinal direction in combination with the interaction between the anchor pads and wings of the medical article to stabilize the medical article, rather than act as a fulcrum. The limited length of the retainer 120 allows access to portions of the medical article that are not retained within the retainer (e.g., a port or similar outwardly extending member). In some embodiments, the retainer 120 secures a portion of a catheter hub near the proximal end of the hub to prevent the hub from being pre-maturely pulled out of the insertion site and to increase stability of the hub relative to the patient.

As shown most clearly in FIG. 7, the lower side of the retainer 120 includes an access or lower opening 150. In some embodiments, the lower opening 150 has generally tapering sides along the longitudinal axis to match generally the shape of the medical article. In other embodiments, the lower opening 150 has generally parallel sides while the channel 140 is tapered to match generally the shape of the medical article. The lower opening 150 may include contouring (e.g., chamfers) along its periphery in order to guide the medical article into the central channel 140 when inserting the medical article into the retainer 120.

The illustrated retainer 120 further comprises at least one retention surface 165(a), 165(b) disposed on a lower side of the inverted channel 140. The retention surface holds at least a portion of the retained medical article within the channel 140. This support can be provided by, for example, an adhesive, a region of the inverted channel which provides a degree of snap-fit with the retained medical article, two or more regions of the inverted channel which provide a degree of snap-fit with the retained medical article, or a combination of the adhesive and a region of snap-fit. The adhesive can be located on one or more surfaces of the retainer 120 that contact the medical article. For example, the adhesive could be located on the surface of the inverted channel or on an abutment.

As shown most clearly in FIGS. 6 and 7, the present embodiment of the retainer 120 includes multiple pairs of retention surfaces 165(a), 165(b) formed on steps 280(a), 280(b) formed within the channel 140. The steps 280(a), 280(b) may be formed along any portion of the channel 140 between the proximal side and distal side of the body 130. The steps may act to narrow a portion of the channel 140. In this way, a portion of a medical article may be received within the steps 280(a), 280(b) while another portion of the medical article may also be received within a different portion of the channel 140.

The corresponding retention surfaces 165(a), 165(b) of each pair lie on opposite sides of the access opening 150 from each other. In this embodiment, the retention surface 165(a) is a portion of the surface that defines the central channel 140 and is located on the lower side of the central channel 140. The retention surface 165(a) is located to one side of the central axis. The other retention surface 165(b) is a portion of the surface that defines the central channel 140 and is located on the lower side of the central channel 140. The retention surface 165(b) is further located to the side of the central axis that is opposite to the retention surface 165(a). Once the medical article is placed in the central channel 140, the retention surfaces 165(a), 165(b) each hold a portion of the retained section of the article within the channel 140.

Pressure can be provided by the retention surfaces 165 which hold the medical article within the retainer 120 in the illustrated embodiment. The retention surfaces 165 provide a degree of snap fit between the retainer 120 and the medical article. The degree of snap-fit can be increased by extending the overall surface of the central channel 140 through an arc of greater than 180°. As shown most clearly in FIG. 6, in one embodiment the arc extends for more than 180° in order to more firmly support the retained portion of the medical article. In the illustrated embodiment, the walls of the central channel 140 extend through an arc of approximately 270°. The length of such an arc provides a snap-fit securement between the central channel 140 on the body member 130 and the secured portion of the medical article. In this way, the medical article can be placed in position prior to attaching the securement device 100 to the patient without concern that the medical article will shift while the healthcare provider is attaching the device 100 to the patient. Additionally, the releasable engagement provided by snap-fit connection also permits the retained portion of the medical article to be readily released from retainer 120.

In the illustrated embodiment, as best seen in FIG. 6, chamfered surfaces 240(a) are formed on the underside of the step 280(a) along one of the lower edges of the access opening 150. A second set of chamfered surfaces 240(b) is formed on the underside of the step 280(b) along the other lower edge of the access opening 150. The portions of the retainer body 130 between these chamfered surfaces 240 and the retention surfaces 165 form hips 270(a), 270(b). In other words, the hips 270 are the portion of the body 130 that is defined by a lower side of the central channel 140 (either the retention surfaces 165(a) on one side of the central axis or the retention surfaces 165(b) on the other side of the central axis), the chamfered surfaces 240, and the sides of the narrow lower opening 150. In one embodiment, the chamfered surfaces 240(a) on one side of the central axis are oblique to the chamber surfaces 240(b) on the other side of the central axis and help guide the medical article into the lower opening 150 and the central channel 140.

The retainer 120 can include a generally rigid structure (at least in comparison to foam or tape) and is principally defined by the body member 130 and the mounting supports 210(a), 210(b). The body member 130, however, preferably is somewhat flexible in nature, due both in part to its structure and to the material used to form the body member 130. Suitably rigid but flexible materials include, for example, but without limitation: plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. However, other materials can be utilized.

The body member 130 and mounting supports 210(a), 210(b) are integrally formed to comprise a unitary retainer. This can be accomplished in any of a variety of ways well known to those skilled in the art. For instance, the entire retainer can be injection molded in order to reduce fabrication costs. The illustrated retainer 120 preferably is formed by injection molding using polyethylene or polypropylene material. The retainer, however, can comprise a non-unitary body member 130 and mounting supports 210(a), 210(b). In this manner, the body member and one or both of the mounting wings are formed separately and then coupled together. Additionally, the body member and mounting supports can have other forms and can have other orientations relative to one another. The body member 130 also can be clear or transparent to facilitate alignment of the retainer 120 with the catheter hub or other medical article during installation.

Each mounting support 210(a), 210(b) preferably comprises a glue dam around a portion of its periphery on its underside. The glue dam restricts adhesive flow beyond an inner edge of the respective mounting support. The outer edge of each mounting support 210(a), 210(b) does not include the glue dam (as best seen in FIG. 7) to allow any excess glue or adhesive to seep out from under the mounting support during the manufacturing process in the lateral direction away from the retainer 120.

The body member 130 of the retainer is attached to the upper surface 170 of the anchor pad 110 via the mounting supports 210(a), 210(b), as is shown in FIG. 2. The body member is desirably secured to the upper surface of the pad by a solvent bond adhesive, such as cyanoacrylate or other bonding material. One such adhesive is available commercially as Part No. 4693 from 3M.

As mentioned above, the medical article includes a pair of outwardly extending wings that interact with lower surfaces of the left and right anchor pads 110. The interaction between the wings and the anchor pads 110 restricts longitudinal, lateral, transverse, and rotational movement of the medical article relative to the retainer 120. When the anchor pads 110 are subsequently secured to the skin of the patient, the medical article is also inhibited from moving substantially in the longitudinal, lateral, transverse, or rotational directions relative to the patient. Longitudinal movement of the medical article is inhibited by engagement between at least one abutment surface on the retainer 120 and a contact surface or mating surface on the medical article as well as by the attachment of the laterally extending wings to the anchor pads 110. The abutment surface on the retainer 120 preferably extends generally normal to the axis of the central channel 140. The abutment surface can be located at or between the distal and proximal ends of the retainer 120. For example, the abutment surface can be either the proximal or distal ends of the retainer (as will be apparent from the embodiments described later). In one embodiment, the abutment surface can be a surface of a step 280 between the proximal and distal ends of the retainer. Moreover, multiple abutment surfaces on the retainer 120 can be employed with each abutment surface being the same or a different type of abutment surface. Additionally, the abutment surface can be used to arrest movement in one longitudinal direction and the shape of the channel can be used to arrest movement in the opposite longitudinal direction. For example, at least a portion of the channel 140 can have a tapering inner surface and the retainer can include an abutment surface in the form of the proximal end of the retainer. The tapering shape and abutment surface cooperate to inhibit longitudinal motion in both longitudinal directions. In such an embodiment, the tapering surface contacts an outer tapering surface of the medical article to limit motion in one direction. Likewise, the proximal end of the retainer abuts with an outwardly extending member on the medical article, for example, a port, to limit motion in the opposite direction.

To further arrest longitudinal motion in the illustrated embodiment, a contact surface in the form of a port extending generally in a transverse direction from the medical article is employed. The port abuts the proximal surface of the body member 130 to inhibit longitudinal motion of the medical article in the distal direction. In some embodiments, the medical article includes a second contact surface that abuts the distal surface of the body member 130 to inhibit longitudinal motion of the medical article in the proximal direction. Further embodiments of the retainer 120 inhibit rotational movement of the installed medical article. This will be discussed in greater detail below.

An embodiment of a port 305 extending generally in a transverse direction from the medical article is described with reference to FIG. 10. The port can be used to provide a medical provider with direct access to the medical line 360 and/or to introduce medicine directly into a patient. In some embodiments, the port 305 includes a septum through which drugs or treatments can be injected and fluid can be drawn many times with less discomfort for the patient than needle punctures. In particular, it can be desirable for the height of the port 305 to be greater than that height of the proximal surface of the body member 130 to ensure that the port contacts or abuts the proximal surface when the medical article is retainer by the retainer. Those of skill in the art will recognize that a port may also abut the distal surface of the body member 130 to inhibit longitudinal motion of the medical article relative to the retainer in the proximal direction.

As shown most clearly in FIGS. 6 and 7, an upper section of the retainer 120 further comprises a depression 135 which forms a finger pad that a healthcare provider can press down upon. The depression 135 encourages the finger to push down on the retainer 120 and discourages the healthcare provided from gripping the retainer 120 on its sides during application. Such a side grip could squeeze or constrict the retainer 120 and make it harder to slip the retainer 120 over the medical article. By pushing down on the retainer 120, this constrictive effect is avoided.

As shown in FIG. 6, a base surface 230 of the retainer 120 is generally planar. In some embodiments, the base surface 230 of the retainer 120 can have a concave curved shape when viewed from the front and rear sides. The degree of curvature can be varied depending on the expected location of usage or application of the securement device 100. It will be appreciated that many common sites for insertion of medical lines which require securement will be located on anatomical regions exhibiting convex curvature, such as a dorsal side of a hand, an arm, a leg, a contact surface, etc. By providing a concave bottom profile to the retainer 120, the retainer will rock less once placed upon the patient via the anchor pads 110(a), 110(b).

FIG. 8 is a side view of the retainer 120 of FIG. 5. As illustrated in FIG. 8, an axis 260 of the central channel 140 lies at an angle with respect to the base surfaces 230 of the retainer 120. The desired angle between the medical article and the patient is created by angling the axis 260 of the central channel 140. This angle is selected in order to align the axis 260 of the channel 140 of the retainer with the desired incident angle with which the medical article is to contact the skin of the patient. A variety of different angles can be used, ranging from about 0° to about 45°, and more preferably from about 5° to about 25°. For instance, for the securement of intravenous catheters, it is desirable for the angle of incidence of the catheter to the skin of the patient to be between about 7° to about 15°. For the securement of arterial catheters, it is desirable for the angle of incident of the catheter to the skin of the patient to be about 12.5°. By angling the axis 260 of the channel 140 at the desired angle, which will depend upon the particular securement application (e.g., securing an arterial catheter, an intravenous catheter, etc.), the proper angle of incidence for a catheter can be maintained.

As shown most clearly in FIG. 5, the body member 130 has a thickness T. The thickness T of the body member 130 in the longitudinal direction can vary in order to maintain a generally constant spring force along the entire length of the retainer 120. In this way, the same amount of force is required to spread the walls of the retainer 120 apart even though in the illustrated embodiment the back end of the retainer 120 spreads more to receive the larger diameter section of a tapered catheter hub. As discussed above the thickness T of the body member can also vary to ensure that a healthcare provider has access to a portion of the secured medical article, for example, access to a port or fitting. In one embodiment, the thickness T of the body member 130 can be less than the distance from a port extending from the catheter hub and extension set cap to allow the body member 130 to secure the hub between the port and extension set cap.

Although certain features of the retainer 120 can be specifically configured for use with a catheter hub, it will be understood by those of skill in the art that such a retainer 120 can be used with other adaptors or medical lines as well. Furthermore, the retainers described herein can be modified to more effectively cooperate with various types of connector fittings and adaptors.

Figure 9:
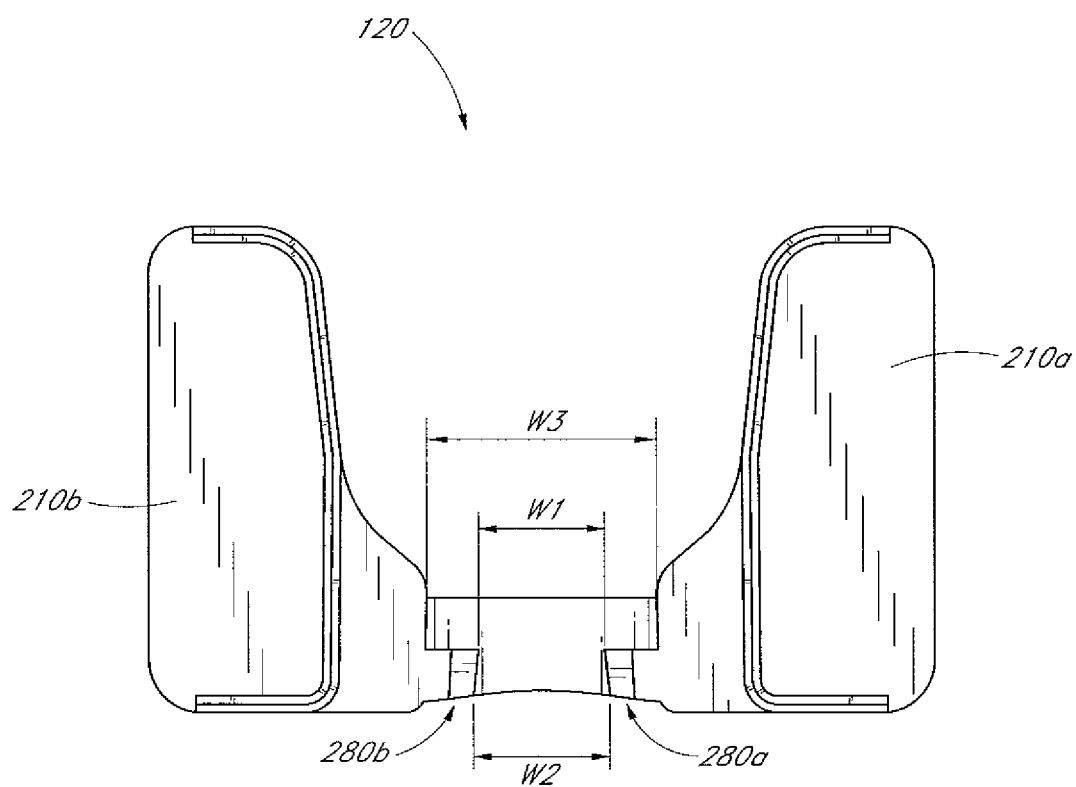
FIG. 9 is a bottom plan view of the retainer of FIG. 5.

FIG. 9 is a bottom plan view of the retainer 120 and illustrates that the distance between the side mounting supports 210(a), 210(b) varies in the region of the retainer 120. Width W1 is measured between the steps 280(a), 280(b) in a lateral direction as shown. Width W2 is measured between the steps 280(a), 280(b) in a lateral direction as shown. Width W3 is measured between the side mounting supports 210(a), 210(b) in a lateral direction as shown. The retainer 120 is designed so that width W1 is less than the width W2 and width W3 is greater than width W2. Width W1 is selected to deter backward insertion of the medical article into the retainer 120. For example, the width W1 could be selected to be smaller than a spin nut or the connector end of the catheter hub. With W1 less than W2, the potential for the medical article being incorrectly inserted into the retainer 120 is reduced. Width W3 is selected to allow the body 130 to receive portions of the medical article that cannot fit within the steps 280(a), 280(b). For example, a portion of a medical article where wings connects to a main body may not fit within the steps 280(a), 280(b) but may still fit within width W3 and be received by at least a portion of the body 130.

Medical Articles

An exemplary medical article for use with the embodiment of the securement device described above will now be described with reference to FIG. 10. The medical article can be a single medical article or a combination of one or more medical articles. In the illustrated embodiment, the medical article includes a pair of outwardly extending wings 301(a), 301(b). Such medical articles can be or include, for example, but without limitation, connector fittings, catheters, catheter hubs, catheter adaptors, fluid supply lines, or other similar articles. FIG. 10 shows a perspective view of a medical article 300 including a catheter hub 430 and a connector fitting 310 with a spin nut 330. The connector fitting 310 is preferably disposed upon the end of a medical line 360 which can be connected to a drip bag, blood monitor, or other fluid related medical apparatus. In some embodiments, the connector fitting 310 may comprise an extension set.

The connector fitting 310 comprises an elongated body 320 which is attached to the end of the medical line 360. The connector fitting 310 also comprises a portion that is tapered along at least part of its longitudinal length so as to allow the end of this region to fit within the tapered conical portion of a catheter hub 430. The tapered portion of the connector fitting 310 also preferably includes a centrally disposed lumen that communicates with the lumen of the medical line. Thus, when the connector fitting 310 is inserted into the catheter hub 430, the lumen of the connector fitting is disposed in fluid communication with the lumen of the catheter hub 430. This provides fluid communication between the medical line 360 and the patient.

A spin nut 330 is disposed upon the connector fitting 310 around the elongated body 320 of the fitting. The spin nut 330 is substantially cylindrical in form and is able to move upon the connector fitting 310. The spin nut 330 is capable of both rotational motion around the axis of the connector fitting and axial motion in both the proximal and distal directions along the length of the elongated body 320 of the fitting. The spin nut 330 also includes internal screw threads which are illustrated with phantom lines in FIGS. 10-12.

Figure 10:
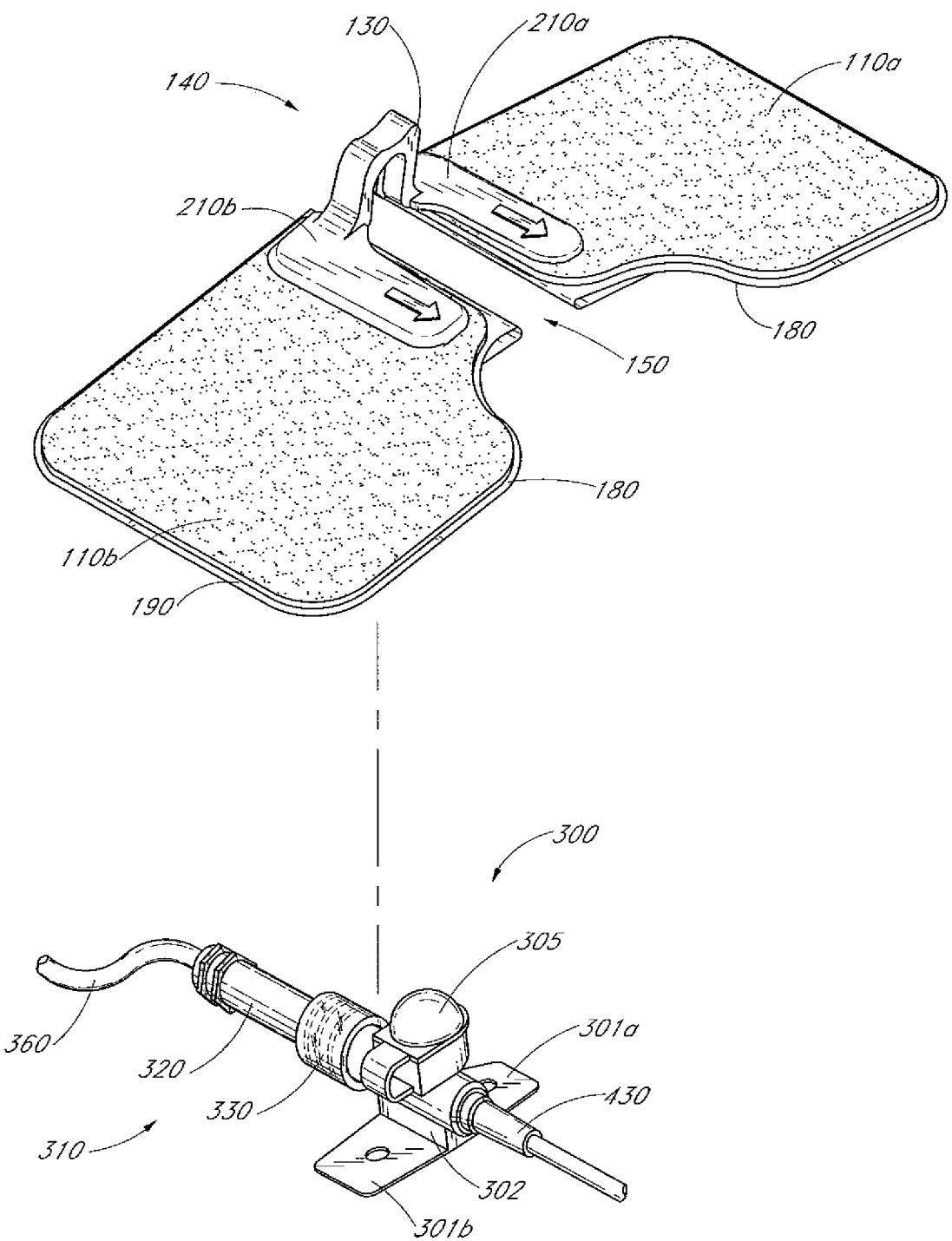
FIG. 10 is a perspective view of the securement system of FIG. 1 positioned above a medical article prior to assembly with the medical article.
Figure 11:
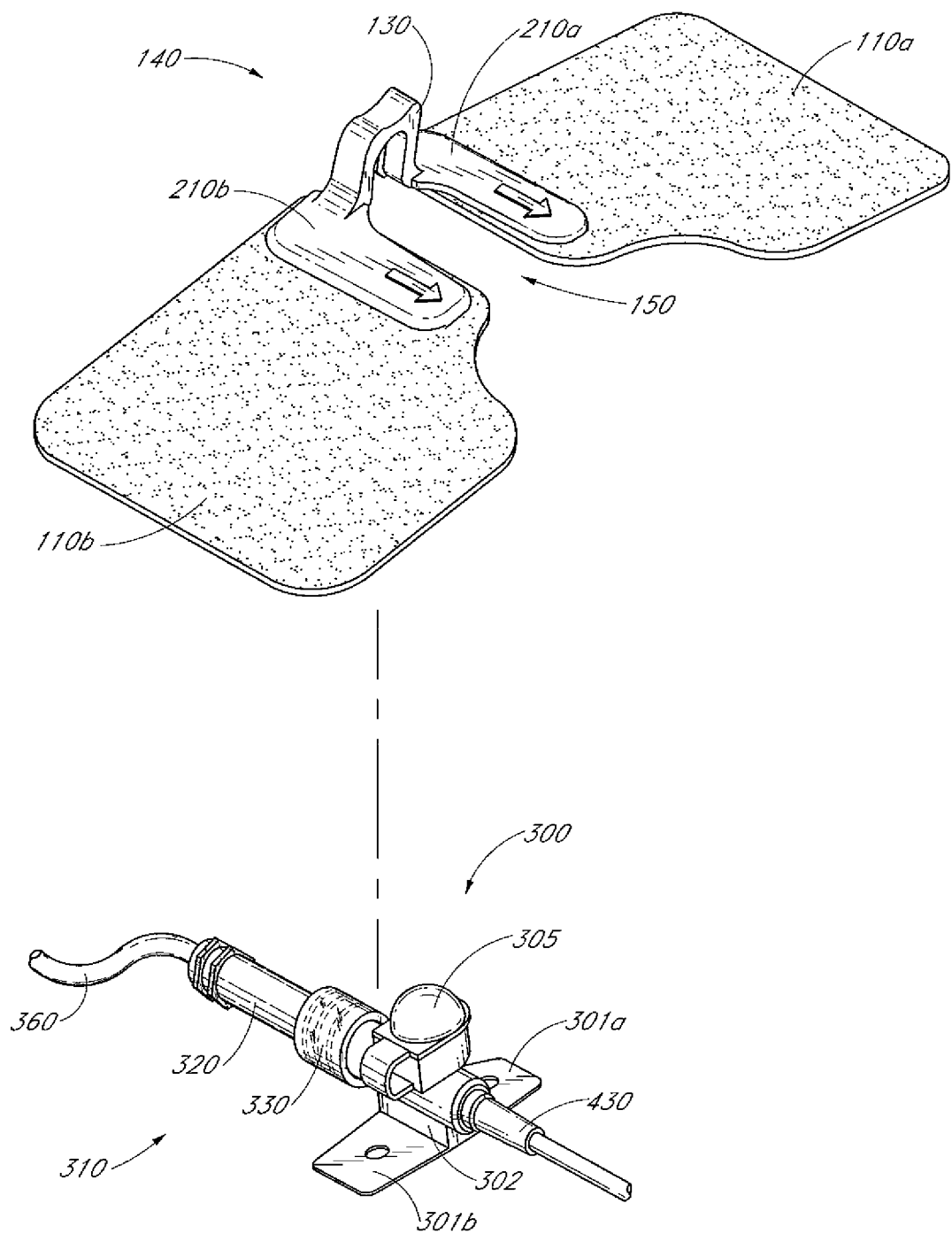
FIG. 11 is similar to FIG. 10 except that release liners have been removed from the anchor pads.

Still referring to FIGS. 10 and 11, the catheter hub 430 includes a body that, in the illustrated embodiment, has a generally conical shape and tapers from a large radius to a smaller radius along its length. A portion of the conical shape may be surrounded by a box 302. The port 305 extends generally in an outward direction from the catheter hub 430 and includes at least one contact surface. Additional contact surfaces can also be disposed upon the connector fitting 310 or catheter hub 430. Those of skill in the art will recognize that the contact surface or surfaces need not have any particular shape or longitudinal thickness.

The pair of outwardly extending wings 301(a), 301(b) extends from box 302 near the bottom side of the box. Additionally, the wings may be generally aligned with the port 305 along the longitudinal axis of the catheter hub 430. The wings may be generally planar so as to comfortably fit between a patient's skin and the anchor pads. The mounting wings and/or anchor pads of the securement device may include one or more recess or receptacles on their bottom surface to receive at least a portion of the wings 301(a), 301(b). In this way, the bottom surface of the wings 301(a), 301(b) can be co-planar with the bottom surfaces of the anchor pads.

The catheter hub 430 also can include an external screw thread on the outside of the conical body near the end with the larger radius. The screw thread can be used in association with the spin nut 330 of the connector fitting 300 in order to securely interconnect the connector fitting 310 and the catheter hub 430.

Figure 12:
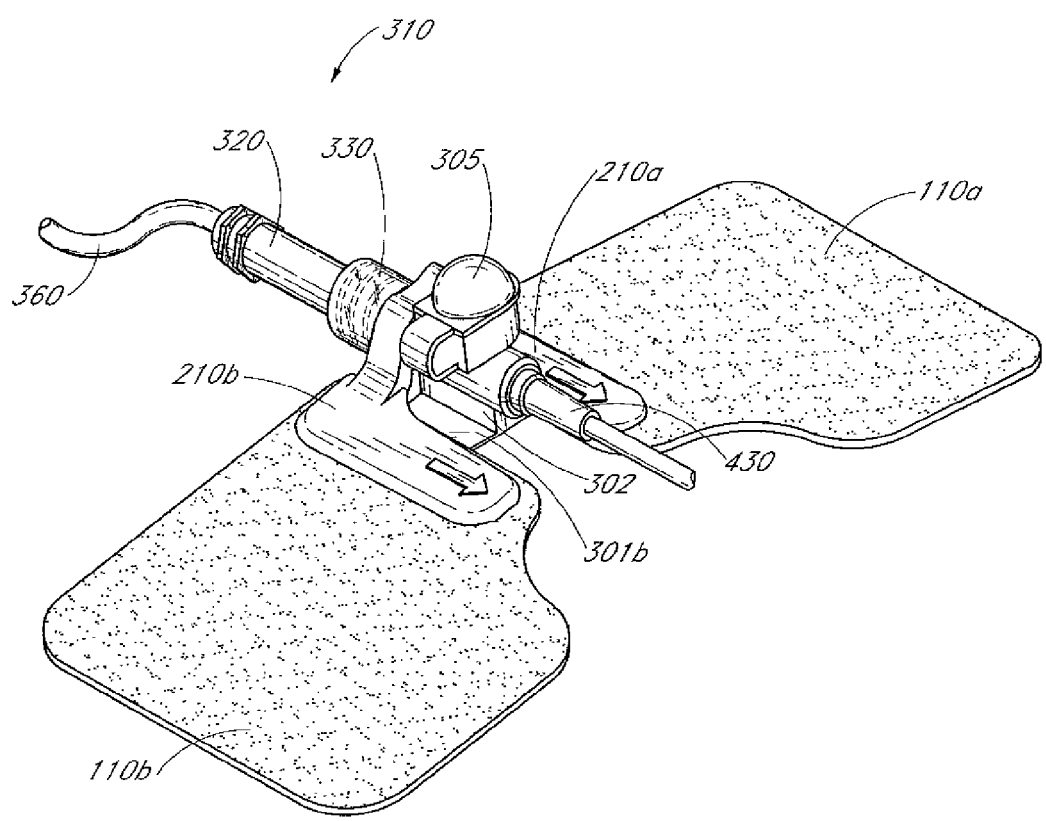
FIG. 12 is a perspective view showing the medical article received within the securement system of FIG. 10.
Figure 13:
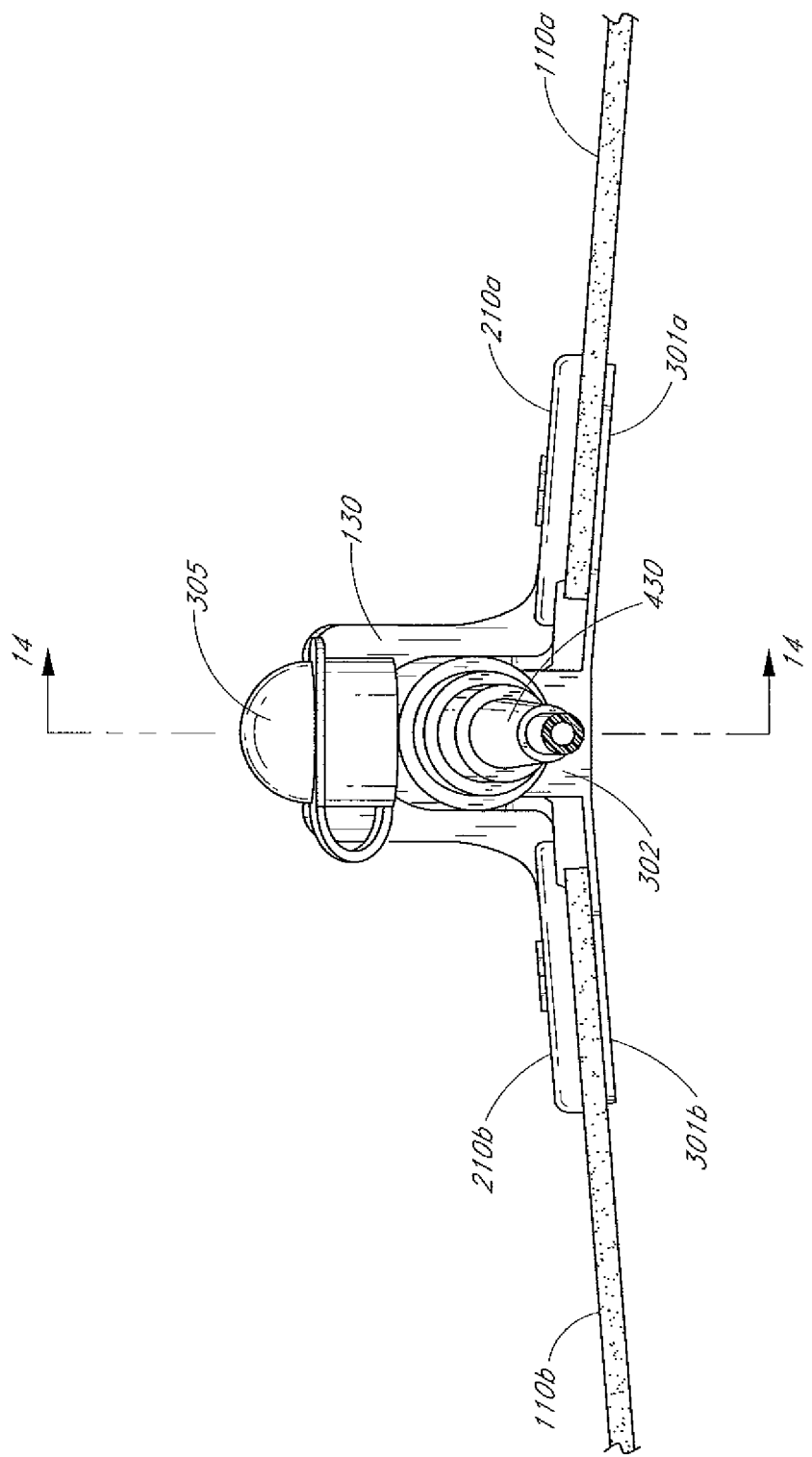
FIG. 13 is a front side view of the securement system and medical article of FIG. 10.

Referring to FIGS. 12 and 13, when the catheter hub 430 is fully installed in the retainer 120, the port 305 extends in a direction away from the longitudinal axis of the catheter hub 430 and can abut the body member 130. The body member 130 may have a thickness configured to secure the portion of the catheter hub 430 between the port 305 and the spin nut 330 without obstructing access to the port. Additionally, the pair of laterally extending wings 301(a), 301(b) are attached to the bottom side of the anchor pads 110(a), 110(b) via an adhesive layer to provide added securement. The pair of wings 301 further limit rotation of the catheter hub 430 when it is installed in the retainer 120 since the wings are attached to the supports 201(a), 210(b).

One advantage of preventing rotation of the catheter hub relative to the retainer is that a healthcare provider can connect or disconnect the connector fitting 310 from the catheter hub 430 without having to grip the retainer, catheter hub, and/or port. Once the healthcare provider rotates the rotates the fitting 310 in either direction the wings 301 contact the supports 210 and the catheter hub 430 is effectively immobilized in that direction such that further rotation of the catheter hub 430 is prohibited while rotation of the fitting 310 is not prohibited. Once immobilized, the healthcare provider can unscrew the spin nut 330 or otherwise disengage the connector fitting from the catheter hub with a single hand. While the use of two hands may be advantageous in certain circumstances when operating the spin nut 330, the retainer 120 allows the healthcare provider to use a single hand.

The retainer 120 can be used with both luer slip and luer lock connector fittings. The retainer 120 is designed such that even with the port 305 positioned at a distal spot on the catheter hub 430, the retainer can fit in the space defined between the port 305 and the spin nut 330 with the spin nut fully engaged. In the illustrated embodiment, a healthcare provider may access the port while the medical article 300 is secured within the retainer 120.

Operation

An exemplary process for coupling a medical article with the securement device described above will now be described with reference to FIGS. 10 through 15.

A preferred method of using the preferred embodiment of the securement device illustrated in FIGS. 1 through 9 will be described in the context of starting an intravenous line. However, the aspects and features of the operational method and the use of the present securement device are not limited to this particular application.

A healthcare provider preferably begins the procedure by inserting an IV catheter into a patient's vein in a known manner and then attaching an intravenous line to the IV catheter though the luer connection. In particular, the healthcare provider inserts the tapered or luer end of the connector fitting 310 into the catheter hub 430 and then turns the spin nut 330 to thread the spin nut 330 over a thread flange disposed at the distal end of the catheter hub 430. This action draws together the two medical article components and releasably interlocks them. The immediate connection of the IV line to the catheter inhibits a back flow of blood through the catheter. The healthcare provider now preferably secures the IV catheter in place on the patient using the securement device 100. In some variations of this method, however, the securement device 100 can be first be attached to one or both of the medical articles (as well as the possibly to the patient) before the healthcare provider makes the connection between the two medical articles.

FIG. 10 is a perspective view of the connector fitting 310 secured to the catheter hub 430, both aligned with the anchor pads 110(a), 110(b) and the retainer. A healthcare provider can secure a medical line 360 and the medical articles to a patient using the above-described securement system 100 or a readily apparent modification thereof. The healthcare provider aligns the central channel 140 of the retainer 120 over the adaptor or catheter hub 430. As shown in FIG. 11, the healthcare provider next removes the release liner 180 from the bottom surface of the anchor pads 110 to expose the adhesive layer for attaching the wings of the medical article to the anchor pads and subsequently attaching the anchor pads to the skin of a patient.

FIG. 12 is a perspective view of the connector fitting 310 secured to the catheter hub 430 with the catheter hub being inserted into the retainer 120. The lower opening 150 in the retainer 120 is pressed over the catheter hub 430 whereby a portion of the catheter hub slides into the channel 140 of the body member 130. The portion of the catheter hub 430 received within the channel 140 may be disposed between the port 305 and the spin nut 330. Depending on the diameter of the catheter hub 430, the steps 280(a), 280(b) can provide a snap-fit connection between the hub and the body member 130.

Figure 14:
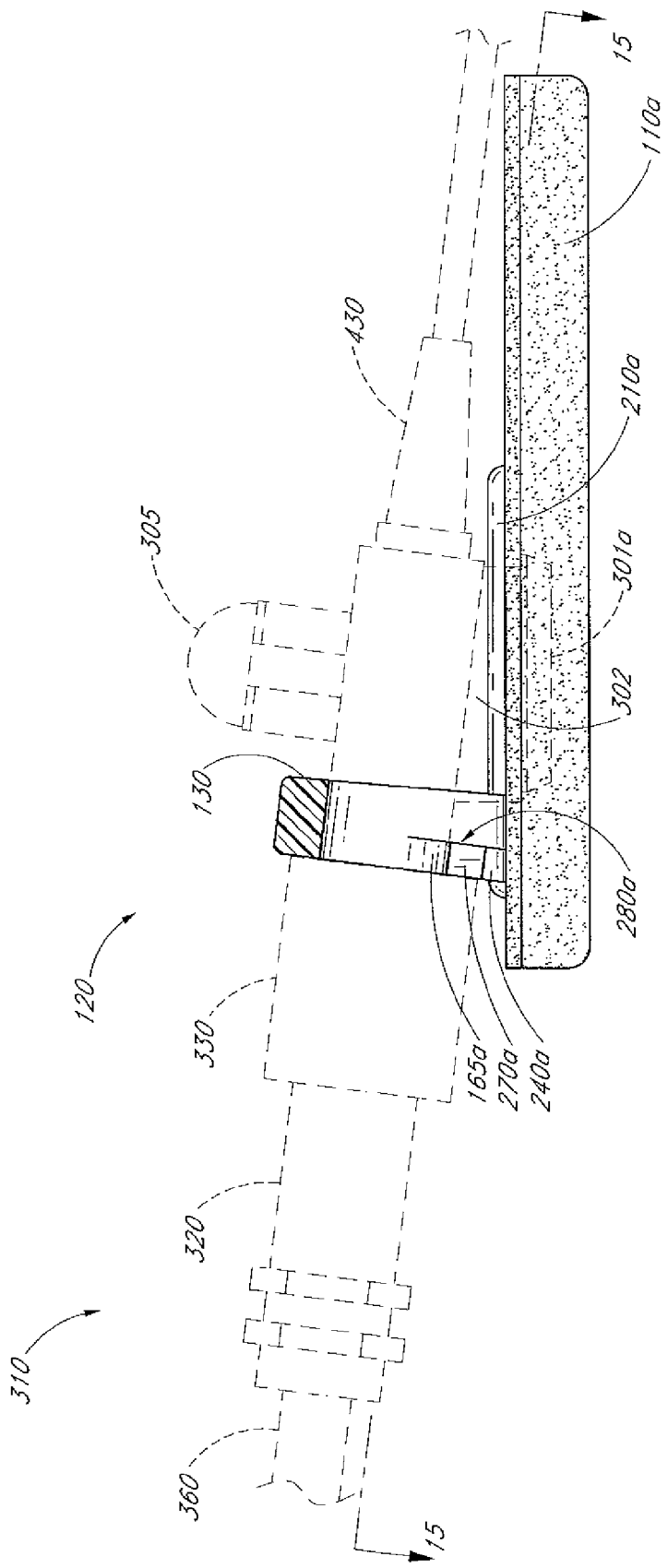
FIG. 14 is a cross-section through the securement system and medical article taken along line 14-14 of FIG. 13.

FIGS. 14 and 15 are cross-sectional views of the connector fitting 310 and catheter hub 430 secured within the retainer 120. As is illustrated in FIG. 14, a portion of the box 302 may be received within the body member 130. As shown in FIG. 15, the portion of the channel on the proximal side of the steps 280(a), 280(b) has a greater diameter than the catheter hub 430. In this way, portions of the catheter hub 430 with different diameters may be secured between the steps 280(a), 280(b) and/or in the channel on the proximal side of the steps 280(a), 280(b). Furthermore, the steps 280(a), 280(b) may prevent longitudinal movement of a received medical article in the distal direction by abutting a portion of the medical article that is disposed on the proximal side of the steps 280(a), 280(b).

The hub preferably includes a contact surface in the form of a port 305 extending from the hub, as shown in the illustrated embodiment. The port 305 contacts or abuts a surface on the body member 130 to inhibit longitudinal movement of the hub relative to the body member. In addition, the pair of wings 301(a), 301(b) extending from the catheter hub 430 is attached to the adhesive layer on the anchor pads 110 to further inhibit longitudinal, rotational, and transverse movement of the hub 430 relative to the retainer 120 in addition to the interaction between the body of the hub and the channel 140.

If used with a connector fitting 310 in which a portion of the connector fitting, such as the spin nut 330, has a greater radial size than the size of the central channel 140 of the retainer 120, the spin nut 330 can act as a contact surface and will inhibit axial motion in one direction through the central channel 140 of the retainer as well. Using the size of the spin nut 330 or other element having greater radial size than the size of the channel is not required for effective operation of the systems described herein; however, such a technique may be an effective form of securement or redundant securement in some applications.

The combination of the channel shape 140 (both the truncated circular shape and the tapering width), the top of the retainer, the interengagement between the body member 130 and the port 305, and the attachment of at least a portion of each wing 301 to the anchor pads 110 arrests movement of the retained section of the medical line in three dimensions: longitudinally, laterally, and transversely. Further, the attachment of the wings 301 to the anchor pads 110 prohibits the hub from 360° rotation while the catheter hub is installed in the retainer 120. The rotational stop provided by the attachment of the wings to the anchor pads allows the healthcare provider to attach and detach the spin nut (and thus the connector fitting) to and front the catheter hub without having the remove the catheter hub from the retainer.

Once the catheter hub or other medical article enters the lower opening 150 of the retainer 120 and a portion of each wing 301 is attached to the adhesive layer on the anchor pads 110(a), 110,(b), the anchor pads are secured to the patient. The central channel 140 of the retainer surrounds an arc length of more than 180° of the medical article. This inhibits any transverse or lateral motion of the medical article relative to the retainer 120. The catheter hub can be inserted into the retainer either before or after the fitting connector is attached to the hub.

The healthcare provider can first remove one portion of the release liner 180 from the anchor pad 110 by gripping the pull tab 190 and pulling the liner 180 away from the lower surface 160 of the anchor pad 110. This exposes the adhesive layer of the anchor pad, which can then be attached to a portion of the laterally extending wings 301(a), 301(b) and then applied to the skin of the patient near the site where the healthcare provider desires to secure the connector fitting 310 or other medical article. The adhesive layer of the second anchor pad which is located in a lateral direction from the first anchor pad can be similarly exposed. The remainder of the release liner 180 for the first and second anchor pads can then be removed and the anchor pad fully attached to the skin of the patient. As a variation, the release liner on one anchor pad can be pulled away and the anchor pad can be fully attached to the patient before attaching the second anchor pad to the patient.

The various embodiments of securement devices and techniques described above thus provide a number of ways to provide safe and releasable securement for medical articles to the skin of a patient. In addition, the techniques described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and systems have been disclosed in the context of certain embodiments and examples, it will be understood by those skilled in the art that these techniques and systems may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above.

What is claimed is:

1. A medical article securement system comprising:
   a medical article comprising,
      an elongated body having a longitudinal axis,
      a pair of wings extending away from the elongated body, and
      a port disposed on the elongated body and forming a contact surface, the port and the pair of wings being disposed along the longitudinal axis of the elongated body;
   at least one anchor pad for contacting both an epidural layer of a patient and at least a portion of the pair of wings; and
   a retainer comprising,
      a body member supported by the at least one anchor pad, the body member having a channel formed therethrough about a channel axis, the channel having a longitudinal length for receiving at least a portion of the elongated body and permitting access to the port at least when the medical article is secured within the channel, the body member having a longitudinal access opening disposed on an underside of the body member to allow at least ingress of the portion of the elongated body into the channel, and
      at least one abutment configured to abut the contact surface on the port so as to inhibit longitudinal movement of the medical article relative to the retainer in at least one direction.

2. The system of claim 1, wherein the at least one abutment is a surface on a proximal end of the body member along the channel axis.

3. The system of claim 1, wherein the at least one abutment is a surface on a distal end of the body member along the channel axis.

4. The system of claim 1, wherein the medical article is a catheter hub.

5. The system of claim 1, wherein the medical article further comprises a spin nut having a diameter greater than a diameter of the elongated body.

6. The system of claim 1, wherein the port comprises a septum.

7. The system of claim 1, wherein the channel has an arc length of greater than 180°.

8. The system of claim 1, wherein the channel has a first tapering shape.

9. The system of claim 8, wherein the channel has a second tapering shape.

10. The system of claim 9, wherein the first tapering shape and the second tapering shape cooperate together when the medical article is inserted into the channel to limit longitudinal movement of the medical article in a first direction.

11. The system of claim 1, wherein the retainer comprises a retention surface for inhibiting transverse motion of the medical article relative to the retainer.

12. The system of claim 11, wherein the retention surface is a movable wall.

13. The system of claim 11, wherein the retention surface is located in the channel.

14. The system of claim 13, wherein the retention surface provides a snap-fit securement with a portion of the medical article.

15. The system of claim 13, wherein the retention surface flexes when the medical article is inserted into the channel.

16. A system for securing a medical article to a patient comprising:
   a medical article comprising,
      an elongated body having a longitudinal axis,
      a pair of wings extending in opposite lateral directions from the elongated body, and
      a port disposed on the elongated body and extending generally in a transverse direction;
   a retainer comprising,
      a body member having a channel formed therethrough about a channel axis, the channel receiving at least a portion of the elongated body and permitting access to the port at least when the medical article is received within the channel, the body member having a longitudinal access opening disposed on an underside of the body member to allow at least ingress of the portion of the elongated body into the channel; and
   a pair of anchor pads supporting the body member, the anchor pads including a lower surface for contacting both an epidural layer of a patient and at least a portion of each wing such that the wings are secured relative to both the epidural layer of the patient and the retainer.

17. The system of claim 16, wherein the body member is spaced from the port along the longitudinal axis when the anchor pads are attached to at least a portion of each wing.

18. The system of claim 16, wherein the port comprises a contact surface and the retainer comprises at least one abutment extending generally normal to the channel axis, the at least one abutment abutting the contact surface of the port so as to inhibit longitudinal movement of the medical article relative to the retainer.

19. The system of claim 18, wherein the contact surface is disposed on a distal side of the port.

20. A method of securing a medical article to a patient, the method comprising:
   providing a medical article comprising an elongated body having a longitudinal axis, a pair of wings and a port extending away from the elongated body, the port defining a contact surface disposed on a distal side of the port;
   providing a retainer comprising a body member and at least one anchor pad, the body member having a channel formed therethrough, the channel being configured to receive the medical article, and at least one abutment extending generally normal to the channel;
   pressing the medical article into the channel through an opening formed on an underside of the retainer such that the port remains accessible and the medical article is inhibited from moving in both transverse and lateral directions,
   abutting the contact surface on the port against the at least one abutment on the retainer so as to inhibit longitudinal motion of the medical article relative to the retainer in a first longitudinal direction; and
   adhering the at least one anchor pad to at least a portion of the pair of wings so as to inhibit longitudinal motion of the medical article relative to the retainer in a second longitudinal direction.

* * * * *